US009353167B2

(12) United States Patent
Deisseroth et al.

(10) Patent No.: US 9,353,167 B2
(45) Date of Patent: *May 31, 2016

(54) METHODS FOR GENERATING IMMUNITY TO ANTIGEN

(71) Applicant: MicroVAX, LLC, Manassas, VA (US)

(72) Inventors: Albert B. Deisseroth, Potomac, MD (US); Yucheng Tang, San Diego, CA (US); Wei-Wei Zhang, San Diego, CA (US); Xiang-Ming Fang, San Diego, CA (US)

(73) Assignee: MicroVAX, LLC, Warrenton, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/478,353

(22) Filed: Sep. 5, 2014

(65) Prior Publication Data

US 2015/0064209 A1 Mar. 5, 2015

Related U.S. Application Data

(63) Continuation of application No. 11/009,533, filed on Dec. 10, 2004, now Pat. No. 8,828,957.

(60) Provisional application No. 60/529,016, filed on Dec. 11, 2003.

(51) Int. Cl.

| | |
|---|---|
| ***A61K 39/00*** | (2006.01) |
| ***A61K 48/00*** | (2006.01) |
| ***C07K 14/47*** | (2006.01) |
| ***C12N 15/86*** | (2006.01) |
| ***C07K 14/705*** | (2006.01) |

(52) U.S. Cl.

CPC ......... *C07K 14/4748* (2013.01); *A61K 39/0011* (2013.01); *C07K 14/70578* (2013.01); *C12N 15/86* (2013.01); *A61K 2039/545* (2013.01); *A61K 2039/6031* (2013.01); *C12N 2710/10343* (2013.01)

(58) Field of Classification Search

USPC ........................... 424/185.1, 192.1; 514/44 R

See application file for complete search history.

(56) References Cited

U.S. PATENT DOCUMENTS

| | | | | |
|---|---|---|---|---|
| 8,119,117 | B2 * | 2/2012 | Deisseroth et al. | 424/93.2 |
| 8,236,295 | B1 * | 8/2012 | Deisseroth et al. | 424/93.2 |
| 8,299,229 | B2 * | 10/2012 | Tang et al. | 536/23.4 |
| 8,501,707 | B2 * | 8/2013 | Tang et al. | 514/44 R |
| 8,828,957 | B2 * | 9/2014 | Deisseroth et al. | 514/44 R |

* cited by examiner

*Primary Examiner* — Janice Li

(74) *Attorney, Agent, or Firm* — Jacob Frank; Glenn Snyder

(57) ABSTRACT

Provided are methods of generating an immune response to an antigen. The method comprises priming an individual by administering an expression vector encoding the antigen. The vector comprises a transcription unit encoding a secretable fusion protein, the fusion protein containing an antigen and CD40 ligand. Administration of a fusion protein containing the antigen and CD40 ligand is used to enhance the immune response above that obtained by vector administration alone. The methods may be used to generate an immune response against cancer expressing a tumor antigen such as a mucin or human papilloma viral tumor antigen and to generate an immune response against an infectious agent. Also provided is a method for simultaneously producing the expression vector and the fusion protein.

5 Claims, 12 Drawing Sheets

FIG. 1

Human MUC-1 Encoding Nucleotide Sequence (SEQ ID NO: 1)

1 ccgctccacc tctcaagcag ccagcgcctg cctgaatctg ttctgccccc tccccaccca
61 tttcaccacc accatgacac cgggcaccca gtctcctttc ttcctgctgc tgctcctcac
121 agtgcttaca gttgttacag gttctggtca tgcaagctct accccaggtg gagaaaagga
181 gacttcggct acccagagaa gttcagtgcc cagctctact gagaagaatg ctgtgagtat
241 gaccagcagc gtactctcca gccacagccc cggttcaggc tcctccacca ctcagggaca
301 ggatgtcact ctggccccgg ccacggaacc agcttcaggt tcagctgcca cctggggaca
361 ggatgtcacc tcggtcccag tcaccaggcc agccctgggc tccaccaccc cgccagccca
421 cgatgtcacc tcagccccgg acaacaagcc agccccgggc tccaccgccc ccccagccca
481 cggtgtcacc tcggccccgg acaccaggcc ggccccgggc tccaccgccc ccccagccca
541 cggtgtcacc tcggccccgg acaccaggcc ggccccgggc tccaccgccc ccccagccca
601 cggtgtcacc tcggccccgg acaccaggcc ggccccgggc tccaccgccc ccccagccca
661 cggtgtcacc tcggccccgg acaccaggcc ggccccgggc tccaccgccc ccccagccca
721 cggtgtcacc tcggccccgg acaccaggcc ggccccgggc tccaccgccc ccccagccca
781 cggtgtcacc tcggccccgg acaccaggcc ggccccgggc tccaccgccc ccccagccca
841 cggtgtcacc tcggccccgg acaccaggcc ggccccgggc tccaccgccc ccccagccca
901 cggtgtcacc tcggccccgg acaccaggcc ggccccgggc tccaccgccc ccccagccca
961 cggtgtcacc tcggccccgg acaccaggcc ggccccgggc tccaccgccc ccccagccca
1021 cggtgtcacc tcggccccgg acaccaggcc ggccccgggc tccaccgccc ccccagccca
1081 cggtgtcacc tcggccccgg acaccaggcc ggccccgggc tccaccgccc ccccagccca
1141 cggtgtcacc tcggccccgg acaccaggcc ggccccgggc tccaccgccc ccccagccca
1201 cggtgtcacc tcggccccgg acaccaggcc ggccccgggc tccaccgccc ccccagccca
1261 cggtgtcacc tcggccccgg acaccaggcc ggccccgggc tccaccgccc ccccagccca
1321 cggtgtcacc tcggccccgg acaccaggcc ggccccgggc tccaccgccc ccccagccca
1381 cggtgtcacc tcggccccgg acaccaggcc ggccccgggc tccaccgccc ccccagccca
1441 cggtgtcacc tcggccccgg acaccaggcc ggccccgggc tccaccgccc ccccagccca
1501 cggtgtcacc tcggccccgg acaccaggcc ggccccgggc tccaccgccc ccccagccca
1561 cggtgtcacc tcggccccgg acaccaggcc ggccccgggc tccaccgccc ccccagccca
1621 cggtgtcacc tcggccccgg acaccaggcc ggccccgggc tccaccgccc ccccagccca
1681 cggtgtcacc tcggccccgg acaccaggcc ggccccgggc tccaccgccc ccccagccca
1741 cggtgtcacc tcggccccgg acaccaggcc ggccccgggc tccaccgccc ccccagccca
1801 cggtgtcacc tcggccccgg acaccaggcc ggccccgggc tccaccgccc ccccagccca
1861 cggtgtcacc tcggccccgg acaccaggcc ggccccgggc tccaccgccc ccccagccca
1921 cggtgtcacc tcggccccgg acaccaggcc ggccccgggc tccaccgccc ccccagccca
1981 cggtgtcacc tcggccccgg acaccaggcc ggccccgggc tccaccgccc ccccagccca
2041 cggtgtcacc tcggccccgg acaccaggcc ggccccgggc tccaccgccc ccccagccca
2101 cggtgtcacc tcggccccgg acaccaggcc ggccccgggc tccaccgccc ccccagccca
2161 cggtgtcacc tcggccccgg acaccaggcc ggccccgggc tccaccgccc ccccagccca
2221 cggtgtcacc tcggccccgg acaccaggcc ggccccgggc tccaccgccc ccccagccca
2281 cggtgtcacc tcggccccgg acaccaggcc ggccccgggc tccaccgccc ccccagccca
2341 cggtgtcacc tcggccccgg acaccaggcc ggccccgggc tccaccgccc ccccagccca
2401 cggtgtcacc tcggccccgg acaccaggcc ggccccgggc tccaccgccc ccccagccca
2461 cggtgtcacc tcggccccgg acaccaggcc ggccccgggc tccaccgccc ccccagccca
2521 cggtgtcacc tcggccccgg acaccaggcc ggccccgggc tccaccgccc ccccagccca
2581 cggtgtcacc tcggccccgg acaccaggcc ggccccgggc tccaccgccc ccccagccca
2641 cggtgtcacc tcggccccgg acaccaggcc ggccccgggc tccaccgccc ccccagccca
2701 cggtgtcacc tcggccccgg acaccaggcc ggccccgggc tccaccgccc ccccagccca
2761 cggtgtcacc tcggccccgg acaccaggcc ggccccgggc tccaccgccc ccccagccca
2821 cggtgtcacc tcggccccgg acaccaggcc ggccccgggc tccaccgccc ccccagccca
2881 tggtgtcacc tcggccccgg acaacaggcc cgccttgggc tccaccgccc ctccagtcca
2941 caatgtcacc tcggcctcag gctctgcatc aggctcagct tctactctgg tgcacaacgg
3001 cacctctgcc agggctacca caaccccagc cagcaagagc actccattct caattcccag
3061 ccaccactct gatactccta ccacccttgc cagccatagc accaagactg atgccagtag
3121 cactcaccat agctcggtac ctcctctcac ctcctccaat cacagcactt ctccccagtt
3181 gtctactggg gtctctttct tttcctgtc ttttcacatt tcaaacctcc agtttaattc
3241 ctctctggaa gatcccagca ccgactacta ccaagagctg cagagagaca tttctgaaat

```
3301 gtttttgcag atttataaac aagggggttt tctgggcctc tccaatatta agttcaggcc
3361 aggatctgtg gtggtacaat tgactctggc cttccgagaa ggtaccatca atgtccacga
3421 cgtggagaca cagttcaatc agtataaaac ggaagcagcc tctcgatata acctgacgat
3481 ctcagacgtc agcgtgagtg atgtgccatt tcctttctct gcccagtctg ggctggggt
3541 gccaggctgg ggcatcgcgc tgctggtgct ggtctgtgtt ctggttgcgc tggccattgt
3601 ctatctcatt gccttggctg tctgtcagtg ccgccgaaag aactacgggc agctggacat
3661 ctttccagcc cgggatacct accatcctat gagcgagtac cccacctacc acacccatgg
3721 gcgctatgtg cccccctagca gtaccgatcg tagcccctat gagaaggttt ctgcaggtaa
3781 cggtggcagc agcctctctt acacaaaccc agcagtggca gccgcttctg ccaacttgta
3841 gggcacgtcg ccgctgagct gagtggccag ccagtgccat tccactccac tcaggttctt
3901 caggccagag cccctgcacc ctgtttgggc tggtgagctg ggagttcagg tgggctgctc
3961 acagcctcct tcagaggccc caccaatttc tcggacactt ctcagtgtgt ggaagctcat
4021 gtgggcccct gaggctcatg cctgggaagt gttgtggggg ctcccaggag gactggccca
4081 gagagccctg agatagcggg gatcctgaac tggactgaat aaaacgtggt ctcccactg
```

FIG 1 (Con't.)

FIG. 2

Human MUC-1 Amino Acid Sequence (SEQ ID NO: 2)

```
       1          11         21         31         41         51
     1 MTPGTQSPFF LLLLLTVLTV VTGSGHASST PGGEKETSAT QRSSVPSSTE KNAVSMTSSV
60
    61 LSSHSPGSGS STTQGQDVTL APATEPASGS AATWGQDVTS VPVTRPALGS TTPPAHDVTS
120
   121 APDNKPAPGS TAPPAHGVTS APDTRPAPGS TAPPAHGVTS APDTRPAPGS TAPPAHGVTS
180
   181 APDTRPAPGS TAPPAHGVTS APDTRPAPGS TAPPAHGVTS APDTRPAPGS TAPPAHGVTS
240
   241 APDTRPAPGS TAPPAHGVTS APDTRPAPGS TAPPAHGVTS APDTRPAPGS TAPPAHGVTS
300
   301 APDTRPAPGS TAPPAHGVTS APDTRPAPGS TAPPAHGVTS APDTRPAPGS TAPPAHGVTS
360
   361 APDTRPAPGS TAPPAHGVTS APDTRPAPGS TAPPAHGVTS APDTRPAPGS TAPPAHGVTS
420
   421 APDTRPAPGS TAPPAHGVTS APDTRPAPGS TAPPAHGVTS APDTRPAPGS TAPPAHGVTS
480
   481 APDTRPAPGS TAPPAHGVTS APDTRPAPGS TAPPAHGVTS APDTRPAPGS TAPPAHGVTS
540
   541 APDTRPAPGS TAPPAHGVTS APDTRPAPGS TAPPAHGVTS APDTRPAPGS TAPPAHGVTS
600
   601 APDTRPAPGS TAPPAHGVTS APDTRPAPGS TAPPAHGVTS APDTRPAPGS TAPPAHGVTS
660
   661 APDTRPAPGS TAPPAHGVTS APDTRPAPGS TAPPAHGVTS APDTRPAPGS TAPPAHGVTS
720
   721 APDTRPAPGS TAPPAHGVTS APDTRPAPGS TAPPAHGVTS APDTRPAPGS TAPPAHGVTS
780
   781 APDTRPAPGS TAPPAHGVTS APDTRPAPGS TAPPAHGVTS APDTRPAPGS TAPPAHGVTS
840
   841 APDTRPAPGS TAPPAHGVTS APDTRPAPGS TAPPAHGVTS APDTRPAPGS TAPPAHGVTS
900
   901 APDTRPAPGS TAPPAHGVTS APDTRPAPGS TAPPAHGVTS APDNRPALGS TAPPVHNVTS
960
   961 ASGSASGSAS TLVHNGTSAR ATTTPASKST PFSIPSHHSD TPTTLASHST KTDASSTHHS
1020
  1021 SVPPLTSSNH STSPQLSTGV SFFFLSFHIS NLQFNSSLED PSTDYYQELQ RDISEMFLQI
1080
  1081 YKQGGFLGLS NIKFRPGSVV VQLTLAFREG TINVHDVETQ FNQYKTEAAS RYNLTISDVS
1140
  1141 VSDVPFPFSA QSGAGVPGWG IALLVLVCVL VALAIVYLIA LAVCQCRRKN YGQLDIFPAR
1200
  1201 DTYHPMSEYP TYHTHGRYVP PSSTDRSPYE KVSAGNGGSS LSYTNPAVAA ASANL
```

METHODS FOR GENERATING IMMUNITY TO ANTIGEN

CROSS REFERENCE TO RELATED APPLICATIONS

This application is a continuation of U.S. patent application Ser. No. 11/009,533 filed on Dec. 10, 2004, which claims priority to U.S. Provisional Patent Application Ser. No. 60/529,016 filed on Dec. 11, 2003, the disclosures of which including the figures are each hereby incorporated herein by reference.

GOVERNMENTAL RIGHTS

This invention was made with Government support under Contract Numbers DAMD17-03-1-0554 and DAMD17-99-1-9457 funded by the U.S. Army Medical Research and Material Command's funding agreement to the Sidney Kimmel Cancer Center, and under funding agreement R43 CA108051 funded by the National Institutes of Health. The Government has certain rights in this invention.

FIELD OF THE INVENTION

The present invention relates to methods of developing immunity against an antigen using an expression vector that expresses a secretable fusion protein comprising an antigen fused to CD40 ligand. The methods also relate to an immunization scheme of priming with the expression vector and boosting with a protein antigen. The invention also relates to an approach for producing the vector and the protein antigen simultaneously in a production cell system.

BACKGROUND OF THE INVENTION

The following discussion of the background of the invention is merely provided to aid the reader in understanding the invention and is not admitted to describe or constitute prior art to the present invention. This application claims priority to U.S. application Ser. No. 60/529,016, filed Dec. 11, 2003, which is incorporated herein in its entirety including the drawings. Applications related to this application are PCT/US03/36237 filed Nov. 12, 2003 entitled "adenoviral vector vaccine" and U.S. provisional patent applications 60/524,925 (filed Nov. 24, 2003), 60/525,552 (filed Nov. 25, 2003), and 60/529,015 (filed Dec. 11, 2003), all of which are incorporated herein in their entirety including the drawings.

The activation of antigen presenting cells (APCs) which includes the dendritic cells (DCs), followed by loading of the antigen presenting cell with relevant antigens, is a requisite step in the generation of a T cell dependent immune response against cancer cells. Once activated and loaded with tumor antigens, DCs migrate to regional lymph nodes (LNs) to present antigens to T cells. Very commonly, these APCs express insufficient amounts of surface activation molecules which are required for optimal activation and expansion of T cell clones competent to recognize tumor antigens. See Shortman, et al., *Stem Cells* 15:409-419, 1997.

Antigen presentation to naive T cells, in the absence of costimulatory molecule expression on the surface of the APC, leads to anergy of the T cells. See Steinbrink, et al. *Blood* 99: 2468-2476, 2002. Moreover, cross-presentation by DCs without $CD4^+$ T cell help also results in peripheral deletion of Ag-specific T cells in regional LNs. See Kusuhara, et al., Eur J Immunol 32:1035-1043, 2002. In contrast, in the presence of $CD4^+$ T cell help, DCs acquire functional ability to cross-prime T cells, resulting in clonal expansion of effector T cells. See Gunzer, et al., Semin Immunol 13:291-302, 2001. This $CD4^+$ T cell help can be replaced with CD40-CD40 ligand (CD40L) interactions. See Luft, et al. Int Immunol 14:367-380, 2002. CD40L is a 33-kDa type II membrane protein and a member of the TNF gene family and is transiently expressed on $CD4^+$ T cells after TCR engagement. See Skov, et al. J Immunol. 164: 3500-3505, 2000.

The ability of DCs to generate anti-tumor immune responses in vivo has been documented in a number of animal tumor models. See Paglia, et al. J Exp Med 183: 317-322, 1996; Zitvogel, et al., J Exp Med. 183: 87-97, 1996. However, DC-mediated induction of immunity represents a major therapeutic challenge. It is considered difficult to ensure that the antigen presenting cells express appropriate adhesion molecules and chemokine receptors to attract DCs to secondary lymphoid organs for priming T cells. See Fong, et al. *J Immunol.* 166: 4254-4259, 2001; Markowicz, et al. *J Clin Invest.* 85: 955-961, 1990; Hsu, et al. *Nat Med.* 2: 52-58, 1996; Nestle, et al. *Nat Med.* 4: 328-332, 1998; Murphy, et al., *Prostate* 38: 73-78, 1999; Dhodapkar, et al. *J Clin Invest.* 104: 173-180, 1999.

SUMMARY OF THE INVENTION

In a first aspect, the invention relates to the use of a fusion protein in developing an immune response to an antigen. In a preferred embodiment, an immune response to an antigen is obtained by administering an expression vector encoding a secretable fusion protein. The vector includes a transcription unit encoding a secretable fusion protein which contains the antigen and CD40 ligand. The fusion protein is also administered before, concurrently or after administration of the vector. Preferably, the fusion protein is administered after the vector.

In one approach, the sequence encoding the antigen in the fusion protein transcription unit is 5' to sequence encoding the CD40 ligand. In another approach, the sequence encoding the CD40 ligand in the fusion protein transcription unit is 5' to sequence encoding the antigen. In a preferred embodiment, the CD40 ligand lacks all or a portion of its transmembrane domain The antigen may be any antigen to which an immune response may be generated in an individual. In preferred embodiments, the antigen is a tumor antigen; the tumor antigen is the E6 or E7 protein of human papilloma virus; the tumor antigen is a mucin antigen, which may be selected from the group consisting of MUC1, MUC2, MUC3A, MUC3B, MUC4, MUC5AC, MUC5B, MUC6, MUC7, MUC8, MUC9, MUC12, MUC13, MUC15, and MUC16; the mucin antigen is from MUC1; the human epidermal growth factor (EGF) like receptor (e.g., HER1, HER2, HER3 and HER4), the antigen is an infectious agent antigen; the infectious agent antigen is a viral antigen; the infectious agent viral antigen is from human papilloma virus; the viral antigen is the E6 or E7 protein of human papilloma virus.

In another aspect, the invention provides methods of treating an individual with cancer that expresses a tumor antigen. The method includes administering the expression vector which includes a transcription unit encoding a secretable fusion protein that contains the tumor antigen and CD40 ligand. The fusion protein is also administered before, concurrently or after administration of the vector. Preferably, the fusion protein is administered after the vector.

In a further aspect, the invention provides a method of generating immunity in a subject to an infectious agent. The method includes administering the expression vector which includes a transcription unit encoding a secretable fusion protein that contains the infectious agent antigen and CD40 ligand. The fusion protein is also administered before, concurrently or after administration of the vector. Preferably, the fusion protein is administered after the vector.

In yet a further aspect, the invention relates to an approach for producing the vector and the fusion protein together in the same host production cell system. In a preferred embodiment, the fusion protein is expressed from the same vector used to generate immunity by vaccination. In this way, both the vector and the fusion protein can be produced simultaneously through a single production system.

In preferred embodiments, the expression vector may be a viral expression vector or a non-viral expression vector; the expression vector may be an adenoviral vector; the vector may be advantageously administered subcutaneously; the vector may be administered on a subsequent occasion(s) to increase the immune response; a signal sequence may be placed upstream of the fusion protein for secretion of the fusion protein; immunity against the antigen may be long lasting and involve generation of cytotoxic $CD8^+$ T cells against antigen expressing cells and the production of antibody to the antigen; the transcription unit may include sequence that encodes a linker between the antigen and the CD40 ligand; suitable linkers may vary in length and composition; the expression vector may include a human cytomegalovirus promoter/enhancer for controlling transcription of the transcription unit; and the CD40 ligand may be a human CD40 ligand.

Abbreviations used herein include “Ad” (adenoviral); “sig” (signal sequence); and “ecd” (extracellular domain).

These and other embodiments are described in detail below.

BRIEF DESCRIPTION OF THE DRAWINGS

FIG. 1 shows the nucleotide sequence encoding human MUC1 (SEQ ID NO:1)

FIG. 2 shows the amino acid sequence of human MUC1 (SEQ ID NO:2).

FIG. 11 compares various boosting strategies following a single subcutaneous administration of Ad-sig-ecdhMUC-1/ ecdCD40L vector on the ability of animals to resist development of a MUC-1 expressing tumor. ecdhMUC-1/ecdCD40L protein in bacterial extract; ecdhMUC-1 linked to the keyhole limpet hemocyaninin (KLH), with or without incomplete Freund's adjuvant; PBS (phosphate buffered saline); and control bacterial extract (bacterial host strain not infected with Ad-sig-ecdhMUC-1/ecdCD40L vector.

DETAILED DESCRIPTION OF THE INVENTION

Figure 3:
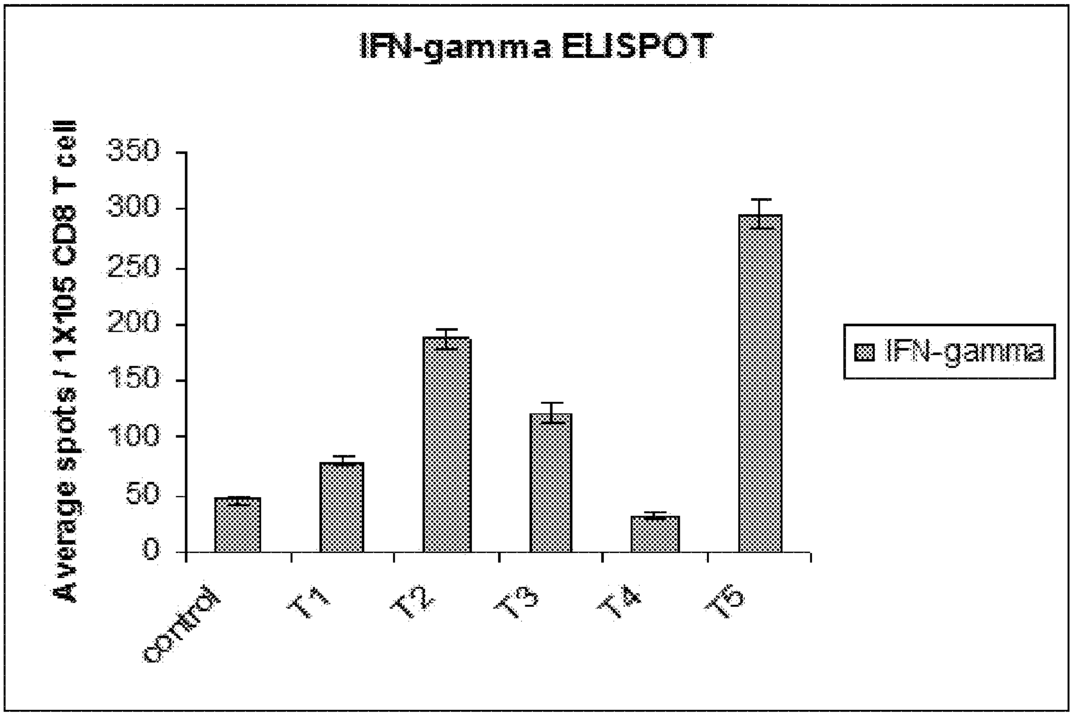
FIG. 3 shows the level of interferon gamma produced in an ELISA spot assay using spleen cells from MUC-1 transgenic animals (hMUC-1.Tg) primed with adenoviral expression vector Ad-K/ecdhMUC1-ΔCtΔTmCD40L and boosted subcutaneously with either expression vector or the mature fusion protein ecdhMUC1-ΔCtΔTmCD40L. The various treatment groups include protein boost seven days after two weekly vector injections (T1), two weeks after two weekly vector injections (T2), one week after one vector injection (T3), and two weeks after one vector injection (T4). In T5, two subcutaneous protein injections (administered two weeks apart) were given starting 7 days after a single vector injection. In Control, two vector injections were given without protein.

In accordance with one aspect of the invention, a method is provided for generating an immune response against an antigen using an expression vector. The vector includes a transcription unit encoding a secretable fusion protein containing an antigen and CD40 ligand. In a preferred embodiment, the transcription unit includes from the amino terminus, a secretory signal sequence, an antigen, a linker and a secretable form of CD40 ligand. In preferred embodiments, the secretable form of CD40 ligand lacks all or substantially all of its transmembrane domain In a preferred approach, the individual is first administered the vector on one or more occasions to generate a primary immune response. The fusion protein is also administered in an effective amount after administration of vector to boost the immune response to the antigen above that obtained with vector administration alone.

The term "in an effective amount" in reference to administering the fusion protein is an amount that generates an increased immune response over that obtained using the expression vector alone. A time interval between administrations is generally required for optimal results. An increase in the immune response may be measured as an increase in T cell activity or antibody production (see e.g., FIGS. 3-5). Generally, at least one week between vector administration and protein boosting is effective although a shorter interval may be possible. An effective spacing between administrations may be from 1 week to 12 weeks or even longer. Multiple boosts may be given which may be separated by from 1-12 weeks or even longer periods of time.

The use of the fusion protein to boost the immune response avoids having to repetitively administer the expression vector which might generate hypersensitivity to multiple injections. The antigen portion of the fusion protein is preferably the fusion protein which is encoded by the transcription unit of the expression vector used in the initial administration. However, the antigen portion of the fusion protein may differ from the encoded antigen provided that there is at least one shared antigenic determinant or epitope common to the antigen of the expression vector and that of the fusion protein used for boosting.

The fusion protein may be prepared in a mammalian cell line system, which is complementary to the vector. Example in the case of adenovirus, the cell line system can be 293 cells that contain the Early Region 1 (E1) gene and can support the propagation of the E1-substituted recombinant adenoviruses. When the adenoviral vectors infect the production cells, the viral vectors will propagate themselves following the viral replication cycles. However, the gene of interest that is carried by the viral vector in the expression cassette will express during the viral propagation process. This can be utilized for preparation of the fusion protein encoded by the vector in the same system for production of the vector. The production of both the vector and the fusion protein will take place simultaneously in the production system. The vector and protein thus produced can be further isolated and purified via different processes.

The fusion protein may be administered parenterally, such as intravascularly, intravenously, intraarterially, intramuscularly, subcutaneously, or the like. Administration can also be orally, nasally, rectally, transdermally or inhalationally via an aerosol. The protein boost may be administered as a bolus, or slowly infused. The protein boost is preferably administered subcutaneously.

The fusion protein boost may be formulated with an adjuvant to enhance the resulting immune response. As used herein, the term "adjuvant" means a chemical that, when administered with the vaccine, enhances the immune response to the vaccine. An adjuvant is distinguished from a carrier protein in that the adjuvant is not chemically coupled to the immunogen or the antigen. Adjuvants are well known in the art and include, for example, mineral oil emulsions (U.S. Pat. No. 4,608,251, supra) such as Freund's complete or Freund's incomplete adjuvant (Freund, Adv. Tuberc. Res. 7:130 (1956); Calbiochem, San Diego Calif.), aluminum salts, especially aluminum hydroxide or ALLOHYDROGEL (approved for use in humans by the U.S. Food and Drug Administration), muramyl dipeptide (MDP) and its analogs such as $[Thr^1]$-MDP (Byers and Allison, Vaccine 5:223 (1987)), monophosphoryl lipid A (Johnson et al., Rev. Infect. Dis. 9:S512 (1987)), and the like.

The fusion protein can be administered in a microencapsulated or a macroencapsulated form using methods well known in the art. Fusion protein can be encapsulated, for example, into liposomes (see, for example, Garcon and Six, J. Immunol. 146:3697 (1991)), into the inner capsid protein of bovine rotavirus (Redmond et al., Mol. Immunol. 28:269 (1991)) into immune stimulating molecules (ISCOMS) composed of saponins such as Quil A (Morein et al., Nature 308:457 (1984)); Morein et al., in Immunological Adjuvants and Vaccines (G. Gregoriadis al. eds.) pp.153-162, Plenum Press, NY (1987)) or into controlled-release biodegradable microspheres composed, for example, of lactide-glycolide compolymers (O'Hagan et al., Immunology 73:239 (1991); O'Hagan et al., Vaccine 11:149 (1993)).

The fusion protein also can be adsorbed to the surface of lipid microspheres containing squalene or squalane emulsions prepared with a PLURONIC block-copolymer such as L-121 and stabilized with a detergent such as TWEEN 80 (see Allison and Byers, Vaccines: New Approaches to Immunological Problems (R. Ellis ed.) pp. 431-449, Butterworth-Hinemann, Stoneman N.Y. (1992)). A microencapsulated or a macroencapsulated fusion protein can also include an adjuvant.

The fusion protein also may be conjugated to a carrier or foreign molecule such as a carrier protein that is foreign to the individual to be administered the protein boost. Foreign proteins that activate the immune response and can be conjugated to a fusion protein as described herein include proteins or other molecules with molecular weights of at least about 20,000 Daltons, preferably at least about 40,000 Daltons and more preferably at least about 60,000 Daltons. Carrier proteins useful in the present invention include, for example, GST, hemocyanins such as from the keyhole limpet, serum albumin or cationized serum albumin, thyroglobulin, ovalbumin, various toxoid proteins such a tetanus toxoid or diptheria toxoid, immunoglobulins, heat shock proteins, and the like.

Methods to chemically couple one protein to another (carrier) protein are well known in the art and include, for example, conjugation by a water soluble carbodiimide such as 1-ethyl-3-(3dimethylaminopropyl)carbodiimide hydrochloride, conjugation by a homobifunctional cross-linker having, for example, NHS ester groups or sulfo-NHS ester analogs, conjugation by a heterobifunctional cross-linker having, for example, and NHS ester and a maleimide group such as sulfosuccinimidyl-4-(N-maleimidomethyl) cyclohexane-l-carboxylate and, conjugation with gluteraldehyde (see, for example, Hermanson, Bioconjugate Techniques, Academic Press, San Diego, Calif. (1996)); see, also, U.S. Pat. Nos. 4,608,251 and 4,161,519).

The term "vector" which contains a transcription unit (aka. "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, herpes simplex viral vectors, and the like. Viral vectors are preferably made replication defective in normal cells. See U.S. Pat. Nos. 6,669,942; 6,566,128; 6,794,188; 6,110,744; 6,133,029.

As used herein, the term "cells" is used expansively to encompass any living cells such as mammalian cells, plant cells, eukaryotic cells, prokaryotic cells, and the like.

The term "adenoviral expression vector" as used herein, refers to any vector from an adenovirus that includes exogenous DNA inserted into its genome which encodes a polypeptide. The vector must be capable of replicating and being packaged when any deficient essential genes are provided in trans. An adenoviral vector desirably contains at least a portion of each terminal repeat required to support the replication of the viral DNA, preferably at least about 90% of the full ITR sequence, and the DNA required to encapsidate the genome into a viral capsid. Many suitable adenoviral vectors have been described in the art. See U.S. Pat. Nos. 6,440,944 and 6,040,174 (replication defective E1 deleted vectors and specialized packaging cell lines). A preferred adenoviral expression vector is one that is replication defective in normal cells.

Adeno-associated viruses represent a class of small, single-stranded DNA viruses that can insert their genetic material at a specific site on chromosome 19. The preparation and use of adeno-associated viral vectors for gene delivery is described in U.S. Pat. No. 5,658,785.

Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described. Kaneda, *Curr Drug Targets* (2003) 4(8):599-602. Reconstituted HVJ (hemagglutinating virus of Japan; Sendai virus)-liposomes can be used to deliver expression vectors or the vectors may be incorporated directly into inactivated HVJ particles without liposomes. See Kaneda, *Curr Drug Targets* (2003) 4(8):599-602. DMRIE/DOPE lipid mixture are useful a vehicle for non-viral expression vectors. See U.S. Pat. No. 6,147,055. Polycation-DNA complexes also may be used as a non-viral gene delivery vehicle. See Thomas et al., *Appl Microbiol Biotechnol* (2003) 62(1):27-34.

The term "transcription unit" as it is used herein in connection with an expression vector means a stretch of DNA that is transcribed as a single, continuous mRNA strand by RNA polymerase, and includes the signals for initiation and termination of transcription. For example, in one embodiment, a transcription unit of the invention includes nucleic acid that encodes from 5' to 3,' a secretory signal sequence, an antigen and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "secretory signal sequence" (aka. "signal sequence," "signal peptide," leader sequence," or leader peptide") as used herein refers to a short peptide sequence, generally hydrophobic in charter, including about 20 to 30 amino acids which is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments the endogenous tumor antigen signal sequence also may be used to direct secretion.

The term "antigen" as used herein refers broadly to any antigen to which an individual can generate an immune response. "Antigen" as used herein refers broadly to molecule that contains at least one antigenic determinant to which the immune response may be directed. The immune response may be cell mediated or humoral or both.

As is well known in the art, an antigen may be protein in nature, carbohydrate in nature, lipid in nature, or nucleic acid in nature, or combinations of these biomolecules. An antigen may include non-natural molecules such as polymers and the like. Antigens include self antigens and foreign antigens such as antigens produced by another animal or antigens from an infectious agent. Infectious agent antigens may be bacterial, viral, fungal, protozoan, and the like.

The term "tumor associated antigen" (TAA) as used herein refers to a protein which is present on tumor cells, and on normal cells during fetal life (onco-fetal antigen), after birth in selected organs, or on many normal cells, but at much lower concentration than on tumor cells. A variety of TAA have been described. An exemplary TAA is a mucin such as MUC1, described in further detail below or the HER2 (neu) antigen also described below. In contrast, tumor specific antigen (TSA) (aka. "tumor-specific transplantation antigen or TSTA) refers to a protein absent from normal cells. TSAs usually appear when an infecting virus has caused the cell to become immortal and to express a viral antigen(s).

An exemplary viral TSA is the E6 or E7 proteins of HPV type 16. TSAs not induced by viruses include idiotypes the immunoglobulin idiotypes associated with \B cell lymphomas or the T cell receptor (TCR) on T cell lymphomas.

An exemplary viral TSA is the E6 or E7 proteins of HPV type 16. HPV can cause a variety of epithelial lesions of the skin and genital tract. HPV related diseases of the genital tract constitute the second leading cause of cancer death among women in the world. These include genital warts, cervical intraepithelial neoplasia (CIN) and cancer of the cervix. The HPV type most commonly associated with high grade CIN and cervical cancer is HPV type 16. The majority of cervical cancers express the non-structural HPV16-derived gene products E6 and E7 oncoproteins. In HPV-induced cervical cancer model, the E6/E7 oncoproteins are required for maintenance of the malignant phenotype and their expression correlates with the transforming potential of HPV16. In addition to using E6 or E7 as the tumor antigen, one may use an antigenic fragment of these proteins instead. An antigenic fragment may be determined by testing the immune response with portions of the molecule such as are predicted to carry an epitope using well known computer algorithms (e.g. Hopp and Woods hydrophobicity analysis).

TSAs not induced by viruses can be idiotypes of the immunoglobulin on B cell lymphomas or the T cell receptor (TCR) on T cell lymphomas. Tumor-associated antigens (TAA) are more common than TSA.

Both TAA and TSA may be the immunological target of an expression vector vaccine. Unless indicated otherwise, the term "tumor antigen" is used herein to refer collectively to TAA and TSA.

The term "mucin " as used herein refers to any of a class of high molecular weight glycoproteins with a high content of clustered oligosaccharides O-glycosidically linked to tandem repeating peptide sequences which are rich in threonine, serine and proline. Mucin plays a role in cellular protection and, with many sugars exposed on the extended structure, effects multiple interactions with various cell types including leukocytes and infectious agents. Mucin antigens also include those identified as CD227, Tumor-associated epithelial membrane antigen (EMA), Polymorphic epithelial mucin (PEM), Peanut-reactive urinary mucin (PUM), episialin, Breast carcinoma-associated antigen DF3, H23 antigen, mucin 1, Episialin, Tumor-associated mucin, Carcinoma-associated mucin. Also included are CA15-3 antigen, M344 antigen, Sialosyl Lewis Antigen (SLA), CA19-9, CA195 and other mucin antigen previously identified by monoclonal antibodies (e.g., see U.S. Pat. No. 5,849,876). The term mucin does not include proteoglycans which are glycoproteins characterized by glycosaminoglycan chains covalently attached to the protein backbone.

At least 15 different mucins have been described including MUC1, MUC2, MUC3A, MUC3B, MUC4, MUC5AC, MUC5B, MUC6, MUC7, MUC8, MUC9, MUC12, MUC13, MUC15, and MUC16 (these may also be designated with a hyphen between "MUC" and the number). The nucleotide sequence and amino acid sequence of these mucins are known. The NCBI and Swiss Prot accession nos. for each of these mucins are as follows: MUC1 (NCBI NM002456, Swiss Prot P15941), MUC2, (NCBI NM002457, Swiss Prot Q02817) MUC3A (NCBI AF113616, Swiss Prot Q02505), MUC3B (NCBI AJ291390, Swiss Prot Q9H195), MUC4 (NCBI NM138299, Swiss Prot Q99102), MUC5AC (NCBI AF043909, Swiss Prot Q8WWQ5), MUC5B (Swiss Prot Q9HC84), MUC6 (NCBI U97698, Swiss Prot Q8N8I1), MUC7 (NCBI L42983, Swiss Prot Q8TAX7), MUC8 (NCBI U14383, Swiss Prot Q12964), MUC9 (NCBI U09550, Swiss Prot Q12889), MUC12 (Swiss Prot Q9UKN1), MUC13 (NCBI NM017648, Swiss Prot Q9H3R2), MUC15 (NCBI NM145650, Swiss Prot Q8WW41), and MUC16 (NCBI AF361486, Swiss Prot Q8WXI7; aka CA125).

There are two structurally and functionally distinct classes of mucins: secreted gel-forming mucins (MUC2, MUC5AC, MUC5B, and MUC6) and transmembrane mucins (MUC1, MUC3A, MUC3B, MUC4, MUC12, MUC17). The products of some MUC genes do not fit well into either class (MUC7, MUC8, MUC9, MUC13, MUC15, MUC16).

The characteristics of particular mucins as TAA in particular cancers is supported by alterations in expression and structure in association with pre-neoplastic and neoplastic lesions (Filipe MI: Invest Cell Pathol 1979, 2:195-216; Filipe MI, Acta Med Port 1979, 1:351-365). For instance, normal mucosa of the stomach is characterized by the expression of MUC1, MUC5A/C, MUC6 mRNA and the encoded immunoreactive protein. Also, high levels of MUC2, MUC3 mucin mRNA and encoded immunoreactive protein are associated with intestinal metaplasia. Gastric cancer exhibits markedly altered secretory mucin mRNA levels compared with adjacent normal mucosa, with decreased levels of MUC5 and MUC6 mRNA and increased levels of MUC3 and MUC4 mRNA. High levels of MUC2 and MUC3 mRNA and protein are detectable in the small intestine, and MUC2 is the most abundant colonic mucin.

Mucins represent diagnostic markers for early detection of pancreatic cancer and other cell types. Studies have shown, that ductal adenocarcinomas (DACs) and tumor cell lines commonly overexpress MUC1 mucin . See Andrianifahanana et al., Clin Cancer Res 2001, 7:4033-4040). This mucin was detected only at low levels in the most chronic pancreatitis and normal pancreas tissues but is overexpressed in all stages of pancreatic cancers. The de novo expression of MUC4 in pancreatic adenocarcinoma and cell lines has been reported (Hollingsworth et al., Int J Cancer 1994, 57:198-203). MUC4 mRNA expression has been observed in the majority of pancreatic adenocarcinoma and established pancreatic cancer cell lines but not in normal pancreas or chronic pancreatitis tissues. MUC 4 expression also has been associated with lung cancer (see Nguyen et al. 1996 Tumor Biol. 17:176-192). MUC5 is associated with metastases in non-small cell lung cancer (see Yu et al., 1996 Int. J. Cancer 69:457-465). MUC6 is overexpressed and MUC5AC is de novo expressed in gastric and invasive DACs (Kim et al., Gastroenterology 2002, 123:1052-1060). MUC7 has been reported as a marker for invasive bladder cancer (see Retz et al. 1998 Cancer Res. 58:5662-5666)

Expression of the MUC2 secreted gel-forming mucin is generally decreased in colorectal adenocarcinoma, but preserved in mucinous carcinomas, a distinct subtype of colon cancer associated with microsatellite instability. MUC2 is increased in laryngeal cancer (Jeannon et al. 2001 Otolaryngol Head Neck Surg. 124:199-202). Another secreted gel-forming mucin, MUC5AC, a product of normal gastric mucosa, is absent from normal colon, but frequently present in colorectal adenomas and colon cancers.

MUC1, also known as episialin, polymorphic epithelial mucin (PEM), mucin like cancer associated antigen (MCA), CA27.29, peanut-reactive urinary mucin (PUM), tumor-associated epithelial mucin, epithelial membrane antigen (EMA), human milk fat globule (HMFG) antigen, MUC1/REP, MUC1/SEC, MUC1/Y, CD227, is the most well known of the mucins. The gene encoding MUC1 maps to 1q21-q24. The MUC1 gene contains seven exons and produces several different alternatively spliced variants. The tandem repeat domain is highly O-glycosylated and alterations in glycosylation have been shown in epithelial cancer cells.

MUC1 mRNA is polymorphic in size. There are presently nine isoforms of MUC1 based on alternate splicing (isoform no.: NCBI accession no.; 1: ID P15941-1, 2: ID P15941-2, 3: ID P15941-3, 4: ID P15941-4, 5: P15941-5, 6: ID P15941-6, 7: ID P15941-7, 8: ID P15941-8, and 9: ID P15941-9).

MUC1 isoform 1 (aka. MUC1/REP) is a polymorphic, type I transmembrane protein containing: 1) a large extracellular domain, primarily consisting of a 20-amino acid (aa) repeat motif (a region known as Variable Number (30-100) of tandem repeats—VNTR); 2) a transmembrane domain; and 3) a 72-aa cytoplasmic tail. During biosynthesis, the MUC1/REP protein is modified to a large extent, and a considerable number of O-linked sugar moieties confer mucin-like characteristics on the mature protein. Soon after translation, MUC1/REP is cleaved into two products that form a tightly associated heterodimer complex composed of a large extracellular domain, linked noncovalently to a much smaller protein including the cytoplasmic and transmembrane domains. The extracellular domain can be shed from the cell. Using Swiss Prot P15941 as a reference (see FIG. 1), the extracellular domain (ecm) of MUC1 isoform 1 represents amino acids 24 to 1158, the transmembrane domain represents 1159-1181, and the cytoplasmic domain represents 1182-1255. The SEA domain represents is 1034-1151 and represents a C-terminal portion of what is referred to as the extracellular domain. The SEA domain of a mucin is generally a target for proteolytic cleavage, yielding two subunits, the smaller of which is associated with the cell membrane.

MUC1 isoform 5 (aka MUC1/SEC) is a form of MUC1 that is secreted by cells. It has an extracellular domain that is identical to that of isoform 1 (MUC1/REP), but lacks a transmembrane domain for anchoring the protein to a cell membrane. MUC1 isoform 7 (aka MUC1/Y) contains the cytoplasmic and transmembrane domains observed in isoforms 1 (MUC1/REP) and 5 (MUC1/SEC), but has an extracellular domain that is smaller than MUC1, lacking the repeat motif and its flanking region (see Baruch A. et al., 1999 Cancer Res. 59, 1552-1561). Isoform 7 behaves as a receptor and binds the secreted isoform 5. Binding induces phosphorylation of isoform 7 and alters cellular morphology and initiates cell signaling through second messenger proteins such as GRB2, (see Zrihan-Licht S. et al., 1995 FEBS Lett. 356, 130-136). It has been shown that β-catenin interacts with the cytoplasmic domain of MUC1 (Yamamoto M. et al., 1997 J. Biol. Chem. 272, 12492-12494).

MUC1 is expressed focally at low levels on normal epithelial cell surfaces. See 15. Greenlee, et al., *Cancer Statistics CA Cancer J.* 50, 7-33 (2000); Ren, et al., *J. Biol. Chem.* 277, 17616-17622 (2002); Kontani, et al., *Br. J. Cancer* 84, 1258-1264 (2001); Rowse, et al., *Cancer Res.* 58, 315 (1998). MUC1 is overexpressed in carcinomas of the breast, ovary, pancreas as well as other carcinomas (see also Gendler S. J. et al, 1990 J. Biol. Chem. 265, 15286-15293). A correlation is found between acquisition of additional copies of MUC1 gene and high mRNA levels ($p<0.0001$), revealing the genetic mechanism responsible for MUC1 gene overexpression, and supporting the role of MUC1 gene dosage in the pathogenesis of breast cancer (Bièche I. et al.,. 1997 Cancer Genet. Cytogenet. 98, 75-80). MUC1 mucin, as detected immunologically, is increased in expression in colon cancers, which correlates with a worse prognosis and in ovarian cancers.

High level expression of the MUC1 antigen plays a role in neoplastic epithelial mucosal cell development by disrupting the regulation of anchorage dependent growth (disrupting E-cadherin function), which leads to metastases. See Greenlee, et al., Cancer Statistics CA Cancer J. 50, 7-33 (2000); Ren, et al. J. Biol. Chem. 277, 17616-17622 (2002). Non-MHC-restricted cytotoxic T cell responses to MUC1 have been reported in patients with breast cancer. See Kontani et al., *Br. J. Cancer* 84, 1258-1264 (2001). Human MUC1 transgenic mice ("MUC-1.Tg") have been reported to be unresponsive to stimulation with human MUC1 antigen. See Rowse, et al., *Cancer Res.* 58, 315 (1998). Human MUC1 transgenic mice are useful for evaluating the development of immunity to MUC1 as a self antigen.

MUC1 protein and mRNA have been found in the ER-positive MCF-7 and BT-474 cells as well as in the ER-negative MDA-MB-231 and SK-BR-3 BCC cells. The mRNA Transcript level was higher in ER+ than in ER− cell lines. MUC1 reacts with intracellular adhesion molecule-1 (ICAM-1). At least six tandem repeats of MUC1 are needed (Regimbald et al., 1996 Cancer Res. 56,4244-4249). The tandem repeat peptide of MUC1 from T-47D BCC was found to be highly O-glycosylated with 4.8 glycosylated sites per repeat, which compares to 2.6 sites per repeat for the mucin from milk.

The term "mucin antigen" as used herein refers to the full length mucin or a portion of a mucin that contains an epitope characterized in being able to elicit cellular immunity using a MUC-CD40L expression vector administered in vivo as described herein. A "mucin antigen" includes one or more epitopes from the extracellular domain of a mucin such as one or more of the tandem repeat motifs associated with the VNTR, or the SEA region. A mucin antigen may contain the entire extracellular domain. Also included within the meaning of "mucin antigen" are variations in the sequence including conservative amino acid changes and the like which do not alter the ability of the antigen to elicit an immune response that crossreacts with a native mucin sequence.

The VNTR consists of variable numbers of a tandemly repeated peptide sequences which differ in length (and composition) according to a genetic polymorphism and the nature of the mucin. The VNTR may also include 5' and 3' regions which contain degenerate tandem repeats. For example, in MUC1, the number of repeats varies from 21 to 125 in the northern European population. In the U.S. the most infrequent alleles contains 41 and 85 repeats, while more common alleles have 60-84 repeats. The MUC1 repeat has the general repeating peptide sequence PDTRPAPGSTAPPAHGVTSA (SEQ ID NO: 3). Underlying the MUC1 tandem repeat is a genetic sequence polymorphism at three positions shown bolded and underlined (positions 2, 3 and 13). The concerted replacement DT→ES (sequence variation 1) and the single replacements P→Q (sequence variation 2), P→A (sequence variation 3), and P→T (sequence variation 4) have been identified and vary with position in the domain (see Engelmann et al., 2001 J. Biol. Chem. 276:27764-27769). The most frequent replacement DT→ES occurs in up to 50% of the repeats. Table 1 shows some exemplary tandem repeat sequences.

TABLE 1

Mucin Tandem Repeat Sequences

| Mucin | Tandem Repeat (SEQ ID NO:) | Mucin source |
|---|---|---|
| MUC1 | PDTRPAPGSTAPPAHGVTSA (SEQ ID NO: 3)<br>PDNKPAPGSTAPPAHGVTSA (SEQ ID NO: 51) | Mammary<br>Pancreatic |
| MUC2 | PTTTPPITTTTTVTPTPTPTGTQT (SEQ ID NO: 4) | Intestinal<br>Tracheobronchial |
| MUC3 | HSTPSFTSSITTTETTS (SEQ ID NO: 5) | Intestinal<br>Gall Bladder |
| MUC4 | TSSASTGHATPLPVTD (SEQ ID NO: 6) | Colon<br>Tracheobronchial |

TABLE 1 -continued

| Mucin Tandem Repeat Sequences | | |
|---|---|---|
| Mucin | Tandem Repeat (SEQ ID NO:) | Mucin source |
| MUC5AC | TTSTTSAP (SEQ ID NO: 7) | Gastric Tracheobronchial |
| MUC5B | SSTPGTAHTLTMLTTTATTPTATGSTATP (SEQ ID NO: 8) | Tracheobronchial Salivary |
| MUC7 | TTAAPPTPSATTPAPPSSSAPG (SEQ ID NO: 9) | Salivary |
| MUC8 | TSCPRPLQEGTPGSRAAHALSRRGHRVHELPTS SPGGDTGF (SEQ ID NO: 10) | Tracheobronchial |

Although a mucin antigen as used herein may comprise only a single tandem repeat sequence motif, it should be understood that the immune response will generally be stronger and more efficiently generated if the vector encodes multiple such repeats. The invention vector preferably encodes mucin tandem repeats from 2-4, more preferably from 5-9, even more preferably from 10-19, yet even more preferably from 20-29, still more preferably from 30-39, and still yet more preferably from 40-50. Tandem repeats greater than 50 are possible and may include the number of such repeats found in natural mucins.

A mucin antigen as this term is used herein also may encompass tandem repeats from different types of mucins. For example, an expression vector may encode tandem repeats from two different mucins, e.g., MUC1 and MUC2. Such a vector also may encode multiple forms of the SEA domain as well or a combination of tandem repeats and one or more SEA domains.

A secretable form of an antigen is one that lacks all or substantially all of its transmembrane domain, if present in the mature protein. For example, in the case of a mucin, the transmembrane domain, if present, is generally about 24 amino acids in length and functions to anchor the mucin or a fragment of the mucin in the cell membrane. A secretable form of MUC1 in which all of the transmembrane domain has been deleted is MUC1 missing residues 1159-1181. A mucin (or antigen) missing substantially all of the transmembrane is one where the domain comprises 6 residues or less of sequence at one end of the transmembrane domain, more preferably less than about 4 residues of sequence at one end of the transmembrane domain, even more preferably less than about 2 residues of sequence on one end of the transmembrane domain, and most preferably 1 residue or less on one end of the transmembrane domain. In a preferred embodiment, the vaccine vector transcription unit encodes a secretable form of a mucin (or antigen) lacking the entire transmembrane domain. A mucin that lacks substantially all of the transmembrane domain rendering the mucin secretable is one that contains no more than six residues of sequence on one end of the domain. The extracellular domain of a human mucin such as MUC1 is denoted herein as "ecdhMUC 1."

It should be understood that a mucin which lacks a functional transmembrane domain may still include all or a portion of the cytoplasmic domain and all or a portion of the SEA region, if present.

A source of DNA encoding the various mucins, and mucin antigens may be obtained from mucin expressing cell lines using a commercial cDNA synthesis kit and amplification using a suitable pair of PCR primers that can be designed from the published mucin DNA sequences. For example, MUC1 or MUC2 encoding nucleic acid may be obtained from CRL-1500 cells, available from the American Type Culture Collection. Mucin encoding DNA also may be obtained by amplification from RNA or cDNA obtained or prepared from human or other animal tissues. For DNA segments that are not that large, the DNA may be synthesized using an automated oligonucleotide synthesizer.

The term "linker" as used herein with respect to the transcription unit of the expression vector refers to one or more amino acid residues between the carboxy terminal end of the antigen and the amino terminal end of CD40 ligand. The composition and length of the linker may be determined in accordance with methods well known in the art and may be tested for efficacy. See e.g. Arai et al., design of the linkers which effectively separate domains of a bifunctional fusion protein. Protein Engineering, Vol. 14, No. 8, 529-532, August 2001. The linker is generally from about 3 to about 15 amino acids long, more preferably about 5 to about 10 amino acids long, however, longer or shorter linkers may be used or the linker may be dispensed with entirely. Longer linkers may be up to about 50 amino acids, or up to about 100 amino acids. A short linker of less than 10 residues is preferred when the mucin antigen is N-terminal to the CD40 ligand.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain at its C-terminus. Unless otherwise indicated the full length CD40L is designated herein as "CD40L," "wtCD40L" or "wtTmCD40L." The form of CD40L in which the cytoplasmic domain has been deleted is designated herein as "ΔCtCD40L." The form of CD40L where the transmembrane domain has been deleted is designated herein as "ΔTmCD40L." The form of CD40L where both the cytoplasmic and transmembrane domains have been deleted is designated herein as "ΔCtΔTmCD40L." The nucleotide and amino acid sequence of CD40L from mouse and human is well known in the art and can be found, for example, in U.S. Pat. No. 5,962,406 (Armitage et al.). Also included within the meaning of CD40 ligand are variations in the sequence including conservative amino acid changes and the like which do not alter the ability of the ligand to elicit an immune response to a mucin in conjunction the fusion protein of the invention.

Murine CD40L (mCD40L) is 260 amino acids in length. The cytoplasmic (Ct) domain of mCD40L extends approximately from position 1-22, the transmembrane domain extends approximately from position 23-46, while the extracellular domain extends approximately from position 47-260.

Human CD40L (hCD40L) is 261 amino acids in length. The cytoplasmic domain of hCD40L extends approximately from position 1-22, the transmembrane domain extends approximately from position 23-46, while the extracellular domain extends approximately from position 47-261.

The phrase "CD40 ligand is missing all or substantially all of the transmembrane domain rendering CD40 ligand secretable" as used herein refers to a recombinant form of CD40 ligand that can be secreted from a cell. The transmembrane domain of CD40L which contains about 24 amino acids in length, functions to anchor CD40 ligand in the cell membrane. CD40L from which all of the transmembrane domain has been deleted is CD40 ligand lacking residues 23-46. CD40 ligand missing substantially all of the transmembrane is one that retains 6 residues or less of sequence at one end of the transmembrane domain, more preferably less than about 4 residues of sequence at one end of the transmembrane domain, even more preferably less than about 2 residues of sequence on one end of the transmembrane domain, and most preferably 1 residue or less on one end of the transmembrane domain Thus, a CD40L that lacks substantially all of the transmembrane domain rendering the CD40L secretable is one that retains no more than six residues of sequence on one end of the domain. Such as CD40L would contain, in addition to the extracellular domain and optionally the cytoplasmic domain, and no more than amino acids 41-46 or 23-28 located in the transmembrane domain of CD40L. In a preferred embodiment, the vaccine vector transcription unit encodes a secretable form of CD40 containing less than 10% of the transmembrane domain. More preferably, CD40L contains no transmembrane domain It should be understood that a CD40L which lacks a functional transmembrane domain may still include all or a portion of the cytoplasmic domain. Likewise, a CD40L which lacks a functional transmembrane domain may include all or a substantial portion of the extracellular domain.

As used herein, an expression vector and fusion protein boost is administered as a vaccine to induce immunity to a tumor antigen. The expression vector and protein boost may be formulated as appropriate with a suitable pharmaceutically acceptable carrier. Accordingly, the vectors or protein boost may be used in the manufacture of a medicament or pharmaceutical composition. Expression vectors and the fusion protein may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, expression vectors and the fusion protein may be prepared for oral administration. Pharmaceutically acceptable solid or liquid carriers may be added to enhance or stabilize the composition, or to facilitate preparation of the vectors. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. When a liquid carrier is used, the preparation may be in the form of a syrup, elixir, emulsion, or an aqueous or non-aqueous suspension.

Expression vectors and the fusion protein may be formulated to include other medically useful drugs or biological agents. The vectors also may be administered in conjunction with the administration of other drugs or biological agents useful for the disease or condition that the invention compounds are directed.

As employed herein, the phrase "an effective amount," refers to a dose sufficient to provide concentrations high enough to generate (or contribute to the generation of) an immune response in the recipient thereof. The specific effective dose level for any particular subject will depend upon a variety of factors including the disorder being treated, the severity of the disorder, the activity of the specific compound, the route of administration, the rate of clearance of the viral vectors, the duration of treatment, the drugs used in combination or coincident with the viral vectors, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. For administration of vectors, the range of particles per administration typically if from about $1\times10^7$ to $1\times10^{11}$, more preferably $1\times10^8$ to $5\times10^{10}$, and even more preferably $5\times10^8$ to $2\times10^{10}$. A vector can be administered parenterally, such as intravascularly, intravenously, intraarterially, intramuscularly, subcutaneously, or the like. Administration can also be orally, nasally, rectally, transdermally or inhalationally via an aerosol. The vectors may be administered as a bolus, or slowly infused. The vector is preferably administered subcutaneously.

As demonstrated herein, vectors encoding tumor associated antigens can induce a protective cellular and humoral immunity against such antigens, including those to which tolerance had developed. Although not wishing to be bound by any theory, it is believed that the invention vaccines generate upon administration a continual local release of the fusion protein composed of the secretable form of the antigen linked to a secretory form of CD40 ligand. As demonstrated herein this facilitates DCs maturation, promoting the development of effective antigen-specific immunity. It is also demonstrated herein that the secretable fusion protein encoding the extracellular domain of human MUC1 and the murine CD40L lacking a transmembrane and cytoplasmic domain (i.e. ecdhMUC1-ΔCtΔTmCD40L) produced from an adenoviral vector dramatically enhanced the potency of the cellular immune response to MUC1 expressing tumor cells. Although not wishing to be bound by any theory, it is believed that subcutaneous injection of the Ad-K-ecdhMUC1-ΔCtΔTmCD40L vector elicited strong MUC1 specific $CD8^+$ T cell-mediated immunity, which prevents the engraftment of cancer cells which express the MUC1 tumor associated antigen.

The immunity generated against the antigens using the invention methods is long lasting. As used herein, the term long lasting means that immunity elicited by the antigen encoded by the vector can be demonstrated for up to 6 months from the last administration, more preferably for up to 8 months, more preferably for up to one year, more preferably up to 1.5 years, and more preferably for at least two years.

In one embodiment, immunity to a mucin TAA can be generated by producing a fusion protein that comprises the extracellular domain of MUC1 fused the amino-terminal end of the CD40 ligand from which the transmembrane and cytoplasmic domains were deleted. Construction of such vector is disclosed in the Examples. As was observed herein, subcutaneous administration of this adenoviral vector mucin vaccine induced a very robust and long lasting $CD8^+$ cytotoxic T cell lymphocyte dependent systemic immune response against cancer cells which carry the MUC1 antigen. The mucin vaccine induced the production of memory cells, which underlie the long lasting immunity.

It was observed that vaccination of mice with the adenoviral vector Ad-sig-ecdhMUC1/ecdmCD40L induced an immune response which suppressed the growth of human MUC1 (hMUC1) antigen positive tumor cells in 100% of mice transgenic for hMUC1 (i.e. these mice are anergic to the hMUC1 antigen prior to the vector injection. See Rowse, et al., *Cancer Res.* 58, 315 (1998). The immune response to the Ad-sig-ecdhMUC1/ecdmCD40L vector lasted up to a year and was shown to be antigen specific. These results demonstrated that the Ad-sig-ecdhMUC1-ecd/ecdCD40L vector can be used for treating epithelial malignancies that express the MUC1.

Subcutaneous injection of the adenoviral MUC1 expression vector increased the level of hMUC1 specific T cells in the spleens of injected hMUC1 transgenic mice by 250 fold. The transgenic mice were allergic to the hMUC1 antigen prior to the vector injection. Thus, vector injection overcame the anergy, inducing a CD8+ T cell dependent systemic Thl immune response that was antigen specific, and HLA restricted. The ability to overcome anergy as observed for vaccination with the adenoviral MUC1 expression vector, was not observed when transgenic mice were vaccinated with purified ecdhMUC1/ecdCD40L-HIS protein.

Although not wishing to be bound by any theory, it is believed that the cells infected in the vicinity of the site of subcutaneous injection of the vector release the tumor antigen/CD40 ligand secretory which is taken up by antigen presenting cells (e.g. DCs) in the vicinity of the infected cells. The internalized tumor antigen would be digested in the proteosome with the resultant tumor antigen peptides trafficking to the endoplasmic reticulum where they would bind to Class I MHC molecules. Eventually, the DCs would present the tumor antigen on the surface in the Class I MHC molecule. Activated, tumor antigen-loaded antigen presenting cells would migrate to lymphocyte bearing secondary organs such as the regional lymph nodes or the spleen. During the two weeks of continuous release of the tumor antigen/CD40 fusion protein, CD8 cytotoxic T cell lymphocytes competent to recognize and kill cells, which carried the tumor associated antigens, would be expanded in the lymph nodes and spleen by the presence of the activated and antigen loaded dendritic cells. The continuous nature of the stimulation and the expansion of the tumor antigen specific cytotoxic T cells by the continuous release from the vector infected cells is believed to generate an immune response which would be greater in magnitude than is possible using a vector which carried a tumor antigen/CD40 ligand which is non-secretory.

The methods of the present invention, therefore, can be used to generate immunity to an antigen which is a self-antigen in an individual. For example, a vector that encodes a mucin antigen from MUC1 can be used to generate $CD8^+$ immunity in a human where the MUC1 mucin antigen is a self antigen. The invention methods also can be used to overcome a state of immunological anergy to an antigen which is a self-antigen.

The following examples serve to illustrate the present invention. These examples are in no way intended to limit the scope of the invention.

EXAMPLES

1. Construction of Adenoviral Expression Vectors

The transcription unit, sig-ecdhMUC1-ΔCtΔTmCD40L of the adenoviral vector encodes a signal sequence (from an Ig kappa chain) followed by the extracellular domain of human MUC1 which is connected via a linker to a fragment of the CD40 ligand (human or mouse) which contains the extracellular domain without the transmembrane or cytoplasmic domains. The fusion protein was engineered to be secreted from vector infected cells by the addition of the kappa chain signal sequence to the amino-terminal end of the fusion protein.

The amino acid sequence of human MUC-1 and the encoding nucleotide sequence are shown in FIGS. 2 and 1, respectively. The encoded MUC1 protein represents 1255 amino acids encoded by nucleotides 74 to 3,841 of SEQ ID NO: 1. The first 23 amino acids (encoded by 74 to 142 of SEQ ID NO:1) represent the MUC1 signal sequence which is removed from the mature mucin. The extracellular domain represents about 1135 amino acids from positions 24 to 1158 (encoded by nucleotides 143 to 3547). The tandem repeat region represents approximately 900 amino acids. Amino acids 74 to 126 (encoded by 229 to 451 of SEQ ID NO:1) represents a 5' degenerate tandem repeat region, amino acids 127 to 945 represents the tandem repeat region (encoded by 452 to 2,908 of SEQ ID NO: 1) while amino acids 946 to 962 represent a 3' degenerate tandem repeat region (encoded by 2809 to 2959 of SEQ ID NO:1). The SEA domain represents amino acids 1034 to 1151, the transmembrane domain represents 1159 to 1181, and the cytoplasmic domain represents 1182 to 1255 (see SEQ ID NO:2).

The transcription unit was introduced into the E1 gene region of the adenoviral vector backbone. After the adenoviral vector particles were generated in HEK 293 cells, the vector DNA was purified by cesium chloride gradient centrifugation. The presence of the signal peptide in the adenoviral vector was confirmed by restriction enzyme analysis and by DNA sequencing.

A transcription unit that included DNA encoding the signal sequence of the mouse IgG kappa chain gene upstream of DNA encoding human MUC-1 ("sig-ecdhMUC-1") was generated by PCR using plasmid pcDNA3-hMUC-1 (gift of Finn O. J., University of Pittsburgh School of Medicine) and the following primers: DNA encoding the mouse IgG kappa chain METDTLLLWVLLLWVPGSTGD (single letter amino acid code) (SEQ ID NO: 11) was prepared by PCR amplification (SEQ ID NOs: 12 ,13 and 14) to generate the full 21 amino acid mouse IgG kappa chain signal sequence (the start codon "ATG" is shown bolded in SEQ ID NO:12).

(SEQ ID NO: 12)
5'-CCACC ATG GAG ACA GAC ACA CTC CTG CTA TGG GTA CTG CTG-3'

(SEQ ID NO: 13)
5'-TC CTG CTA TGG GTA CTG CTG CTC TGG GTT CCA GGT TC-3'

(SEQ ID NO: 14)
5'-TG CTC TGG GTT CCA GGT TCC ACT GGT GAC GAT G-3'

(SEQ ID NO: 15)
5'-GGT TCC ACT GGT GAC GAT GTC ACC TCG GTC CCA

-continued

GTC-3'
(forward primer for MUC-1 repeat region)

(SEQ ID NO: 16)
5'-GAGCTCGAG ATT GTG GAC TGG AGG GGC GGT G-3'
(reverse primer for MUC-1 repeat region)

sig-ecdhMUC-1 with the upstream kappa signal sequence was generated by four rounds of PCR amplification (1st round: primers SEQ ID NOs 15 and 16; 2nd round: primer SEQ ID NOs 14 and 16; 3rd round: primer SEQ ID NOs 13 and 16; 4th round: primer SEQ ID NOs 12 and 16). The sig-ecdhMUC-1 encoding DNA was cloned into the pcDNA™ 3.1 TOPO vector (Invitrogen, San Diego, Calif.) forming pcDNA-sig-ecdhMUC-1.

pShuttle -ΔCtΔTmCD40L (no signal sequence and murine CD40L) was prepared as follows: Plasmid pDC406-mCD40L was purchased from the American Type Culture Collection. A pair of PCR primers (SEQ ID NOs: 17 and 18) was designed to amplify the mouse CD40 ligand from position 52 to 260 (i.e., without the cytoplasmic and transmembrane domains) and include sequence encoding a linker (indicated as "+spacer") at the 5' end of the amplicon.

Mouse ΔCtΔTmCD40L + spacer forward primer (MCD40LSPF) (CD40L sequence italicized; cloning site underlined and bolded):

(SEQ ID NO: 17)
5'-CCGCTCGAGAACGACGCACAAGCACCAAAATCAAAGGTCGAAG

AGGAAGTA-3'.

Mouse CD40L reverse primer (MCD40LR; cloning site underlined)

(SEQ ID NO: 18)
5'-GCGGGCC CGCGGCCGCCGCTAG TCTAGA GAG TTT GAG TAA

GCC AAA AGA TGA G-3'

The forward primer MCD40LSPF encodes a 10 residue spacer (LENDAQAPKS; single letter code; SEQ ID NO: 19) to be located between the mucin and the CD40 ligand (mCD40L) of the transcription unit. PCR performed using the forward and reverse primers (SEQ ID NOs 17 and 18) and plasmid pDC406-mCD40L as the template resulted in PCR fragment "space+ΔCtΔTMCD40L", which was inserted into the plasmid pcDNA-sig-ecdhMUC1 after restriction endonuclease digestion with XbaI (TCTAGA) and Xho I (CTCGAG). This vector is designated pcDNA-sig-ecdhMUC1/ΔCtΔTmCD40L. A vector was produced that was otherwise the same except that it encoded full length CD40L rather than the truncated form. This vector was made using a CD40 forward primer that annealed to the starting codons of murine CD40L. This vector is designated pShuttleCD40L (no signal sequence).

The sig-ecdhMUC1/ΔCtΔTmCD40L encoding DNA was cut from the pCDNA3TOPO vector using HindIII-XbaI restriction and inserted into pShuttle-CMV (see Murphy et al., *Prostate* 38: 73-78, 1999) downstream of the CMV promoter. The plasmid is designated pShuttle-sig-ecdhMUC1-ΔCtΔTmCD40L. Thus, the transcription unit sig-ecdhMUC1-ΔCtΔTmCD40L encodes the mouse IgG kappa chain secretory signal followed by the extracellular domain of human MUC1 followed by a 10 amino acid linker with (NDAQAPK; residues 3-9 of SEQ ID NO: 19) followed by murine CD40 ligand residues 52-260.

In some vectors, the mouse HSF1 trimer domain was added between the ecdhMUC1 encoding DNA and ΔCtΔTm CD40L by PCR using plasmid pcDNA-sig-ecdhMUC1/ΔCtΔTmCD40L and the following primers:

(SEQ ID NO: 20)
5'-AAC AAG CTC ATT CAG TTC CTG ATC TCA CTG GTG

GGATCC AAC GAC GCA CAA GCA CCA AAA TC-3'.

(SEQ ID NO: 21)
5'-AGC CTT CGG CAG AAG CAT GCC CAG CAA CAG AAA

GTC GTC AAC AAG CTC ATT CAG TTC CTG-3'.

(SEQ ID NO: 22)
5'AAT GAG GCT CTG TGG CGG GAG GTG GCC AGC CTT

CGG CAG AAG CAT G-3'.

(SEQ ID NO: 23)
5'GAT ATC CTC AGG CTC GAG *AAC GAC GCA CAA GCA*

*CCA AAA* GAG AAT GAG GCT CTG TGG CGG G-3'.

(SEQ ID NO: 18)
5'-GCGGGCC CGCGGCCGCCGCTAG TCTAGA GAG TTT GAG

TAA GCC AAA AGA TGA G-3'.

HSF1/ΔCtΔTm CD40L with the trimer domain sequence was generated by four rounds of PCR amplification (1st round: primers SEQ ID NOs 23 and 18; 2nd round: primer SEQ ID NOs 22 and 18; 3rd round: primer SEQ ID NOs 21 and 18; 4th round: primer SEQ ID NOs 20 and 18). The HSF1/ΔCtΔTm CD40L encoding DNA was cloned into pcDNA-sig-hMUC-1 restriction sites XbaI (TCTAGA) and Xho I (CTCGAG). The sequence between MUC1 and mCD40L is as follows:

(SEQ ID NO: 24)
L E N D A Q A P K E N E A L W R E V A S F R Q K

H A Q Q Q K V V N K L I Q F L I S L V G S N D A

Q A P K S, wherein the underlined segment is the trimer sequence which is bonded by the linker LENDAQAPK (SEQ ID NO:25) and NDAQAPKS (SEQ ID NO:26).

In some vectors, a His tag encoding sequence was added to the end of the ΔCtΔTm CD40L and was generated by PCR using Plasmid pDC406-mCD40L (purchased from the American Type Culture Collection) and the following primers:

(forward primer)

(SEQ ID NO: 27)
5'-CCG CTCGAGAACGACGCACAAGCACCAAAATCA*AAGGTCGAAGAGG*

*AAGTA*-3'

(reverse primer)

(SEQ ID NO: 28)
5'-ATG GTG ATG ATG ACC GGT ACG GAG TTT GAG TAA GCC

AAA AGA TGA GAA GCC-3'

(poly His region encoded by nucleotides in the box)

(SEQ ID NO: 29)
5'-GTGC *TCTAGA* TCA *GAATTC* [ATG GTG ATG GTG ATG ATG]

ACC GGT ACG GAG-3'

Vector/ΔCtΔTm CD40L/His with the His tag sequence was generated by 2 rounds of PCR amplification (1st round: primers 1+2; $2^{nd}$ round: primer 1+3). The/ΔCtΔTmCD40L/His encoding DNA was cloned into pcDNA-sig-ecdhMUC-1 restriction sites XbaI (TCTAGA) and Xho I (CTCGAG).

The recombinant adenoviral vectors were generated using the AdEasy vector system (Stratagene, San Diego, Calif.). Briefly the resulting plasmid pShuttle-sig-ecdhMUC1-ΔCtΔTmCD40L, and other control adenoviral vectors were linearized with Pme I and co-transformed into *E. coli* strain BJ5183 together with pAdEasy-1, the viral DNA plasmid. Recombinants were selected with kanamycin and screened by restriction enzyme analysis. The recombinant adenoviral construct was then cleaved with Pac Ito expose its Inverted Terminal Repeats (ITR) and transfected into 293A cells to produce viral particles. The titer of recombinant adenovirus was determined by the Tissue culture Infectious Dose ($TCID_{50}$) method.

Primers for amplifying human ΔCtΔTmCD40L+ spacer using a human CD40 ligand cDNA template are set forth below.

```
Human ΔCtΔTmCD40L + spacer forward primer
(HCD40LSPF) (CD40L sequence italicized):
                                        (SEQ ID NO: 30)
5'-CCG
CTCGAGAACGACGCACAAGCACCAAAATCAGTGTATCTTCATAGAAGGTTG
GACAAG-3'

Human CD40L reverse primer (HCD40LR)
                                        (SEQ ID NO: 31)
5'-CCCTCTAGA TCAGAGTTTGAGTAAGCCAAAGGAC-3'
```

These primers will amplify a ΔCtΔTmCD40L+spacer which encodes 47-261 of human CD40L. The forward primer HCD40LSPF encodes a 10 residue spacer (LENDAQAPKS; single letter code; SEQ ID NO: 19) to be located between the tumor antigen and the CD40 ligand (hCD40L) of the transcription unit. PCR performed using the forward and reverse primers (SEQ ID NOs 30 and 31) and Plasmid pDC406-hCD40L as the template results in PCR fragment "space+ΔCtΔTmCD40L(human)," which is inserted into the plasmid pcDNA-sig-ecdhMUC1 after restriction endonuclease digestion with XbaI (TCTAGA) and Xho I (CTCGAG). The sig-ecdhMUC1/ΔCtΔTmCD40L (human) encoding DNA was cut from the pCDNA3TOPO using HindIII-XbaI restriction and inserted into pShuttle-CMV (see Murphy et al., *Prostate* 38: 73-78, 1999) downstream of the CMV promoter. This vector is designated pShuttle sig-ecdhMUC1/ΔCtΔTmCD40L(human). Modification of pShuttle sig-ecdhMUC1/ΔCtΔTmCD40L(human) to include the ecdhMUC1 upstream of the human CD40 ligand sequence was accomplished essentially as described above for the murine CD40 ligand encoding vectors. Thus, the transcription unit sig-ecdhMUC1-ΔCtΔTmCD40L(human) encodes the kappa secretory signal followed by the extracellular domain of human MUC1 followed by a 10 amino acid linker (NDAQAPK; residues 3-9 of SEQ ID NO:19) followed by human CD40 ligand residues 47-261.

In an alternative approach, DNA encoding the human growth hormone signal sequence MATGSRTSLLLAFGLLCLPWLQEGSA (single letter amino acid code) (SEQ ID NO: 32) could be used in place of the kappa chain signal sequence.

2. Overcoming Anergy to MUC1 in MUC1 Transgenic Mice a) Cytokine Production of Adenoviral Infected DCs Bone marrow derived DCs was harvested from hMUC-.Tg transgenic mice at 48 hours after exposure to the adenoviral vectors. The cells were exposed to vector at MOI 100, and plated in 24-well plates at $2\times10^5$ cells/ml. After incubation for 24 hours at 37° C., supernatant fluid (1 ml) was harvested and centrifuged to remove debris. The level of murine IL-12 or IFN-gamma released into the culture medium was assessed by enzyme-linked immunoadsorbent assay (ELISA) using the mouse IL-12 p70 or IFN-gamma R & D Systems kits.

Bone marrow derived DCs contacted with the Ad-sig-ecdmMUC1-ΔCtΔTCD40L (murine) vector showed significantly increased the levels of interferon gamma and IL-12 cytokines from DCs harvested from the hMUC-.Tg transgenic mice at 48 hours after exposure to the vector. In contrast, virtually no cytokines were detected from restimulated DC's from animals immunized with an adenoviral vector that encoded the extracellular domain of hMUC 1 but without fusion to a secretable form of CD40L. These results indicate that the ecdhMUC1/ecdmCD40L (murine) fusion protein forms functional trimers and binds to the CD40 receptor on DCs.

b) Evaluation of Trimer Formation by ecdhMUC1-HSF1-ΔCtΔTmCD40L Fusion Protein Expressed from Ad-sig-ecdhMUC1-HSF1-ΔCtΔTmCD40L-HIS Trimerization of ecdhMUC1-HSF1-ΔCtΔTmCD40L-HIS fusion protein was evaluated following release from cells transformed with Ad-sig-ecdhMUC1-HSF1-ΔCtΔTmCD40L-HIS vector. The expressed fusion protein was purified from the supernatant of 293 cells exposed to the vector using a His Tag purification kit. Nondenaturing gel electrophoresis showed a molecular weight consistent with trimer formation.

c) Effect of Ad-sig-ecdhMUC1-ΔCtΔTmCD40L Vector Injection on Establishment of MUC1 Expressing Cancer Cells.

hMUC-1.Tg mice injected subcutaneously with the Ad-sig-ecdhMUC1-ΔCtΔTmCD40L (murine) vector were resistant to engraftment by the hMUC1 positive LL2/LL1hMUC1 mouse cancer cells. Control animals not injected with vector were not resistant to the growth of the same cells. Also, hMUC-1.Tg mice injected with the Ad-sig-ecdhMUC1/ecdCD40L (murine) vector were not resistant to engraftment by parental cell line (LL2/LL1), which does not express MUC1.

hMUC-1.Tg mice injected intravenously with ecdhMUC1-ΔCtΔTmCD40L (murine) protein were not resistant to engraftment by the hMUC1 positive LL2/LL1hMUC1 mouse cancer cells. Furthermore, hMUC-1.Tg mice injected with Ad-sig-ecdhMUC1-ΔCtΔTmCD40L (murine) vector lived longer than did control vector injected mice subsequently administered the LL2/LL1hMUC1 cell line.

3. Cellular Mechanisms Underlying Breakdown of Anergy a) Cytokine Release from Vaccinated vs. Non Vaccinated Mice.

A population of splenic $CD8^+$ T lymphocytes was obtained seven days following Ad-sig-ecdhMUC1-ΔCtΔTmCD40L (murine) vector administration was obtained by depleting $CD4^+$ T lymphocytes using $CD4^+$ antibody coated magnetic beads. The isolated $CD8^+$ T lymphocytes released over 2,000 times the level of interferon gamma as did $CD8^+$ T cells from MUC-1.Tg mice administered a control vector (without MUC1).

b) Cytotoxicity Assay

Splenic T cells collected from hMUC-1.Tg mice 7 days following administration of Ad-sig-ecdhMUC1-ΔCtΔTmCD40L (murine) vector were cultured with hMUC1 antigen positive LL2/LL1hMUC1 cancer cells in vitro for 7 days. The stimulated splenic T cells were mixed in varying ratios with either the hMUC1 positive LL2/LL1hMUC1 cells or the hMUC1 negative LL2/LL1 cancer cells. The results showed that T cells from Ad-sig-ecdhMUC1-

ΔCtΔTmCD40L (murine) vector vaccinated mice were cytotoxic only for the cancer cells expressing hMUC1.

c) Ad-sig-ecdhMUC1-ΔCtΔTmCD40L vector Injection Overcomes Resistance to Expansion of hMUC1 Specific T Cells.

DCs obtained in vitro from bone marrow cells were exposed to the Ad-sig-ecdhMUC1-ΔCtΔTmCD40L (murine) vector for 48 hours. Splenic $CD8^+$ T cells, obtained from hMUC-1.Tg transgenic mice 7 days following no vector injection or subcutaneous injection with the Ad-sig-ecdh-MUC1-ΔCtΔTmCD40L (murine) vector, were mixed in a 1/1 ratio with the Ad-sig-ecdhMUC1/ecdCD40L (murine) vector-infected DCs. The ERK1/EK2 proteins, the endpoint of the Ras/MAPK signaling pathway, were phosphorylated in the CD8+ T cells isolated from Ad-sig-ecdhMUC1-ΔCtΔTmCD40L vector injected hMUC-1.Tg transgenic mice following 45 minutes of in vitro exposure to Ad-sig-ecdh-MUC1-ΔCtΔTmCD40L (murine) vector infected DCs. In contrast no increase in phosphorylation of ERK1 and ERK2 proteins was seen in CD8 positive T cells from unvaccinated hMUC-1.Tg mice. These results demonstrate that CD8 positive T cells from MUC-1.Tg transgenic mice vaccinated with the Ad-sig-ecdhMUC1-ΔCtΔTmCD40L (murine) vector were no longer anergic to MUC1.

4. Production of the Fusion Protein and Vector

The tumor antigen fusion protein was produced directly from an adenoviral vector that carries the expression cassette of the fusion gene encoding the fusion protein. The production cells (e.g. 293 cell line) at 80% confluency in growth medium were infected with the viral vector at the ratio of 10-100 viral particles per cell. The infected cells were further cultured for 48-72 hours, when the viral vectors propagated in the cells and the tumor antigen fusion proteins were expressed in the cells and secreted into culture media. The infected cells were collected when 70-90% of them showed cytopathic effect (CPE). The cell culture media was collected separately. Cell lysates were prepared through 3-time freeze-and-thaw cycles. The viral particles were isolated via the standard procedure (19). The tumor antigen fusion proteins were purified through affinity chromatograph from the collected cell media 5. Amplification of the Immune Response by Protein Boosting The relative value of protein boosting with the tumor antigen fusion protein versus boosting with the adenoviral expression vector was evaluated.

hMUC-1.Tg animals were primed by subcutaneous administration of Ad-K/ecdhMUC1-ΔCtΔTmCD40L vector as described. The protein boost constituted 10 micrograms of ecdhMUC-1/ecdCD40L fusion protein injected subcutaneously. The time of protein boosting and comparison with vector was evaluated in various treatment groups shown in table 2.

TABLE 2

| Immunization Schedule | | | | |
|---|---|---|---|---|
| Testing Group | Week 1 | Week 2 | Week 3 | Week 4 |
| Control | Vector | Vector | Nothing | Nothing |
| Treatment 1 (T1) | Vector | Vector | Protein | Nothing |
| Treatment 2 (T2) | Vector | Vector | Nothing | Protein |
| Treatment 3 (T3) | Vector | Protein | Nothing | Nothing |
| Treatment 4 (T4) | Vector | Nothing | Protein | Nothing |
| Treatment 5 (T5) | Vector | Protein | Nothing | Protein |
| Negative Control | Nothing | Nothing | Nothing | Nothing |

Spleen cells from the different groups were isolated and evaluated by the ELISPOT assay for interferon gamma positivity. As seen in FIG. 3. two subcutaneous protein injections at a 14 day interval beginning one week after the initial vector injection showed the greatest elevation of the frequency of positive T cells as compared to no treatment or compared with one or two vector injections without protein boost. The next highest elevation of the frequency of interferon gamma positive T cells was with the T3 group (one protein injection 7 days following the initial vector injection).

Figure 4:
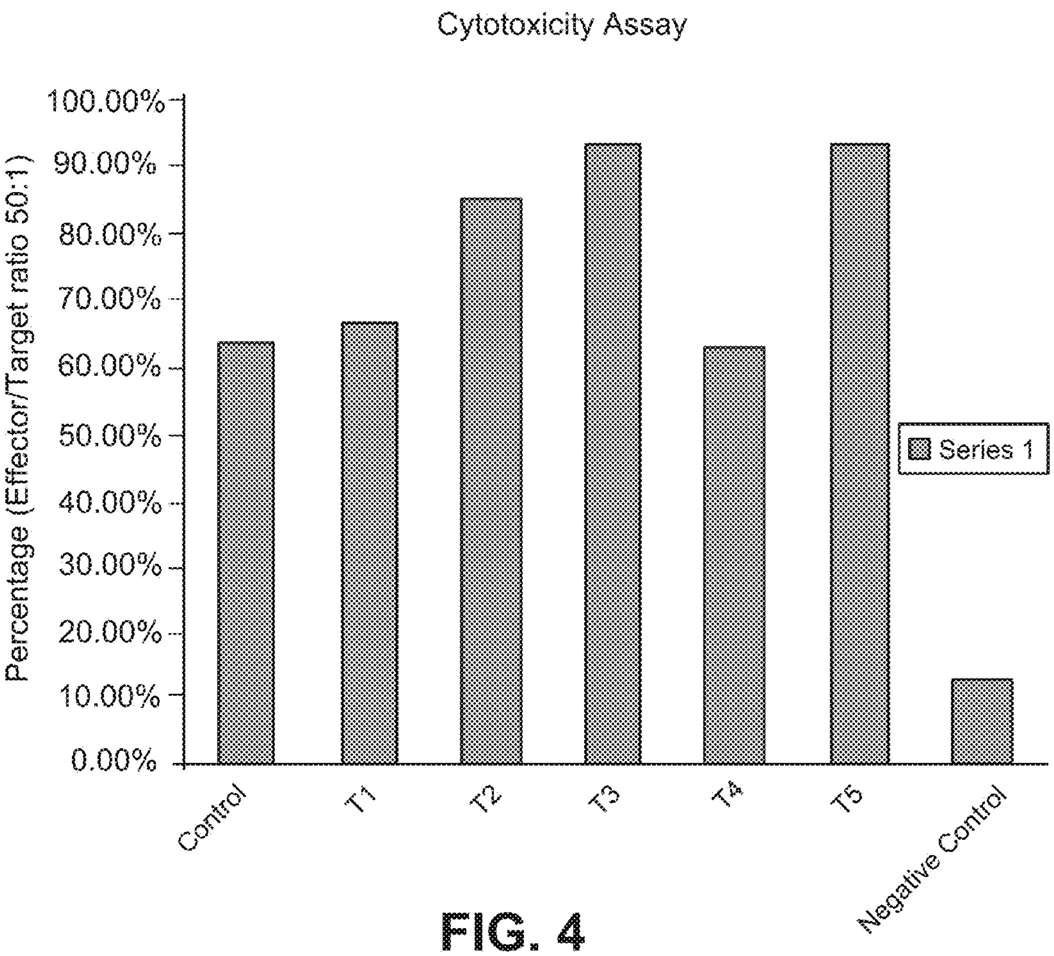
FIG. 4 shows the level of T cell cytotoxicity from MUC-1 transgenic animals (hMUC-1.Tg) primed with adenoviral expression vector Ad-K/ecdhMUC1-ΔCtΔTmCD40L and boosted subcutaneously with either expression vector or the mature fusion protein ecdhMUC1-ΔCtΔTmCD40L. The various treatment groups are as described in FIG. 3.

Cytotoxic T cells development in the various immunization groups was also evaluated (FIG. 4). Spleen cells from the various treatment groups were stimulated in vitro for 5 days with a hMUC-1 positive cell line (LL1/LL2hMUC-1). CD8 T cells were isolated and mixed with the target cells (LL1/LL2hMUC-1) in a 50/1 ratio. Cytotoxic activity generally followed the ELISPOT assay results, with the T5 group showing the greatest increase levels of LL1/LL2hMUC-1 specific cytotoxic T cell activity. The level of cytotoxicity seen with T cells from the T5 group was nine fold that seen with the negative control group.

Serum from the animals in the various treatment groups were evaluated for anti-ecdhMUC1-ΔCtΔTmCD40L specific antibodies in an ELISA. Briefly, microwells coated with the ecdhMUC1-ΔCtΔTmCD40L protein were incubated with test mouse serum, washed and bound mouse antibody identified using a secondary rat anti-mouse antibody conjugated to horseradish peroxidase.

Figure 5:
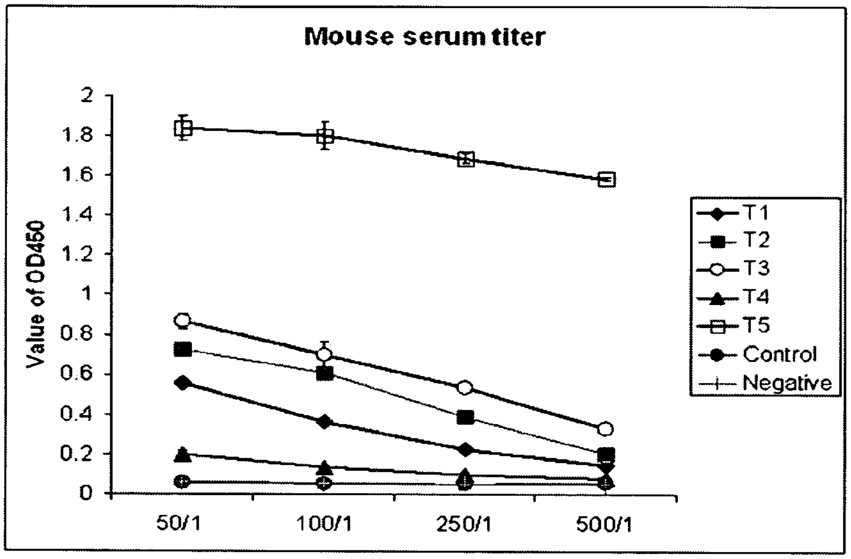
FIG. 5 shows the level of antibody against fusion protein ecdhMUC1-ΔCtΔTmCD40L in serum of MUC-1 transgenic animals (hMUC-1.Tg) primed with adenoviral expression vector Ad-K/ecdhMUC1-ΔCtΔTmCD40L and boosted subcutaneously with either expression vector or the mature fusion protein ecdhMUC1-ΔCtΔTmCD40L. The various treatment groups are as described in FIG. 3. Antibodies were detected in an ELISA. Microwell plates coated with the fusion protein ecdhMUC1-ΔCtΔTmCD40L were reacted with serum, washed and bound mouse antibody detected using rat anti-mouse antibody conjugated to horseradish peroxidase.

FIG. 5 shows a dramatic increase in the level of antibodies to the ecdhMUC1-ΔCtΔTmCD40L fusion protein generated by the treatment with one vector injection and two protein injections spaced at a 14 day interval. The increase in the anti-ecdhMUC1-ΔCtΔTmCD40L antibodies following the T5 treatment was 2 fold greater than with any of the other treatment group.

The results from these assays demonstrate that protein boosting is superior to vector boosting in generating cytotoxic T cell activity against tumor antigen expressing cells as well as antibody responses to the tumor antigen. The overall best results with protein boosting were obtained using a single injection of adenoviral expression vector followed one week later with a subcutaneous protein boost, which is repeated two weeks later by another protein boost.

Antibodies in serum from vaccinated hMUC-1.Tg mice were evaluated for binding to cancer biopsy tissue specimens. Tissue microarrays containing normal breast and breast cancer tissue sections were obtained commercially. Tissue was contacted with serum from transgenic mice immunized with Ad-K/ecdhMUC-1/ΔCtΔTm CD40L vector and boosted later with ecdhMUC-1/ΔCtΔTm CD40L protein. The arrays were washed and then exposed to a horseradish peroxidase (HRP) secondary antibody which recognizes mouse IgG antibody. As a control, the serum was exposed first to a hMUC-1 peptide from the antigenic repeat of the hMUC-1 domain (same as used for the protein boost).

Serum from the vaccinated mice bound to the breast epithelial cells from biopsy specimens of cancerous epithelial cells. No binding to the intervening fibroblast or stromal cells were observed. Serum from normal mice showed no reaction.

Serum from hMUC-1.Tg mice vaccinated with the Ad-sig-hMUC-1/ecdCD40L followed by two subsequent administrations of protein sc-hMUC-1/ecdCD40L reacted with biopsy specimens from human prostate cancer on tissue microarray slides.

To determine specificity of the serum generated antibodies for the hMUC-1 repeat, serum from vaccine immunized animals described above was mixed with increasing amounts of a peptide containing the amino acid sequence from the hMUC-1 repeat. The mixture was then applied to the microarray slides and evaluated for reactivity. A peptide with the same amino acids as the hMUC-1 repeat but with the sequence scrambled ("scrambled peptide") was added to serum from vaccinated animals as a control. The hMUC-1 peptide blocked binding of the antibodies in vaccinated serum to the breast cancer epithelial cells. No blocking was seen for the scrambled peptide. These suggests demonstrate that the vector prime/protein boost vaccination induced a hMUC-1 specific humoral response reactive with MUC-1 expressed by biopsy specimens of human breast cancer epithelial cells.

Tumor immunity in protein boosted mice was evaluated. hMUC-1.Tg animals were primed by subcutaneous administration of Ad-K/ecdhMUC1-ΔCtΔTmCD40L vector as described or were immunized with one or two administrations of the ecdhMUC1-ΔCtΔTmCD40L fusion protein. Animals were then challenged with LL2/LL1hMUC-1 tumor cells.

Figure 6:
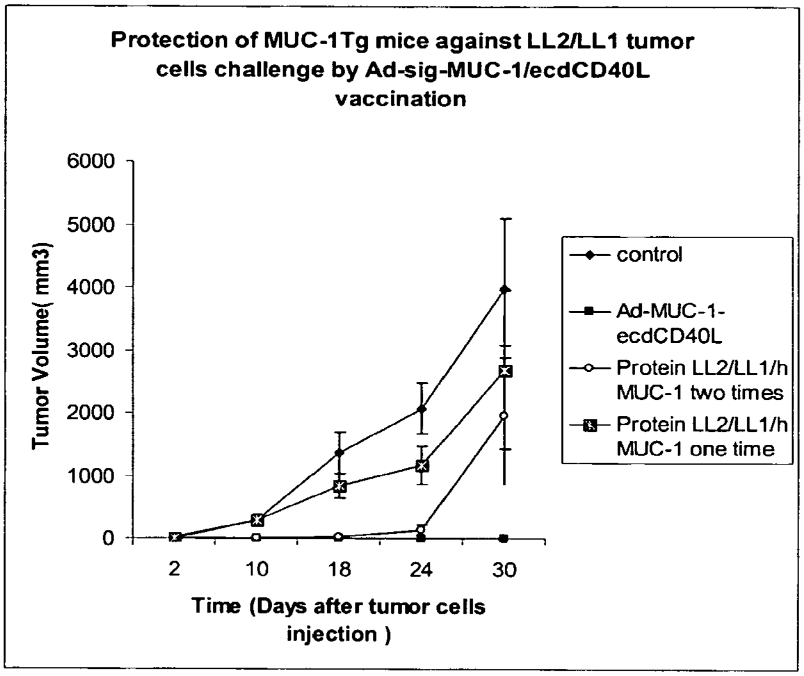
FIG. 6 shows the level growth of MUC1 expressing tumor cells (LL2/LL2hMUC-1) in MUC-1 transgenic animals (hMUC-1.Tg) administered adenoviral expression vector Ad-K/ecdhMUC1-ΔCtΔTmCD40L versus one or two subsequent administrations of fusion protein ecdhMUC1-ΔCtΔTmCD40L.

FIG. 6 shows that mice vaccinated with the Ad-K/ecdhMUC1-ΔCtΔTmCD40L vector survived longer than 120 days (solid bold line), whereas all mice not vaccinated with the Ad-sig-ecdhMUC-1/ecdCD40L vector died by 50 days (broken line). These results show that the vector injections induced a suppression of the growth of the LL2/LL1hMUC-1 cell line in the hMUC-1.Tg mice.

The specificity of tumor growth suppression for the hMUC-1 antigen was evaluated by comparing rejection of the LL2/LL1hMUC-1 cell line (which is positive for the hMUC-1 antigen) with the LL2/LL1 cell line, which is otherwise identical except for the absence of the hMUC-1 antigen. The results showed subcutaneous injection of the adenoviral vector completely suppressed the growth of the LL2/LL1hMUC-1 cell line but did not the same cells which do not express MUC-1.

Tumor growth suppression was evaluated using combinations of vector and protein administration. Three combinations of Ad-sig-ecdhMUC-1/ecdCD40L vector and ecdhMUC-1/ecdCD40L protein were administered to hMUC-1.Tg mice before challenge with LL2/LL1hMUC-1 tumor cells. VVV=three Ad-sig-ecdhMUC-1/ΔCtΔTm CD40L vector subcutaneous injections administered on days 1, 7 and 21; PPP=three ecdhMUC-1/ΔCtΔTm CD40L protein subcutaneous injections administered on days 1, 7 and 21; or VPP=a single Ad-sig-ecdhMUC-1/ΔCtΔTm CD40L vector subcutaneous injection followed at days 7 and 21 by ecdhMUC-1/ΔCtΔTm CD40L protein subcutaneous injections. See FIG. 7 for further details. The mice were challenged one week later with a subcutaneous injection of five hundred thousand LL2/LL1hMUC-1 lung cancer cells, and two weeks later with an intravenous injection of 500,000 LL2/LL1hMUC-1 tumor cells. The size of the subcutaneous tumor nodules at day were measured by caliper at multiple time points to determine the effect of the various vaccine schedules on the growth of the LL2/LL1hMUC-1 cells as subcutaneous nodules. The metasteses were measured by total lung weight following sacrifice.

Figure 7:
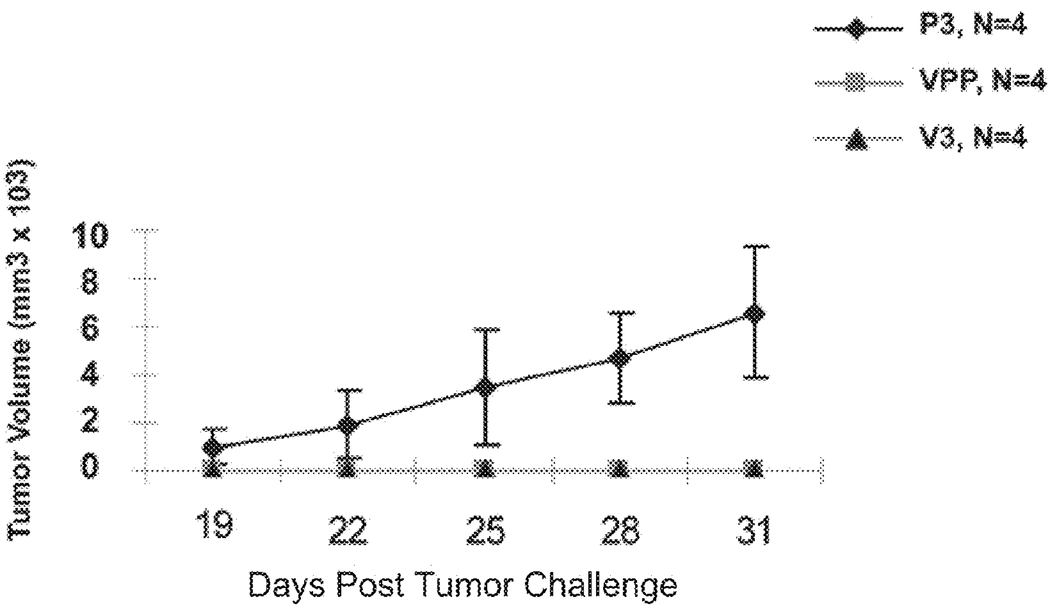
FIG. 7 demonstrates tumor prevention in animals immunized with Ad-sig-ecdhMUC-1/ΔCtΔTmCD40L vector and ecdhMUC-1/ΔCtΔTm CD40L protein. VVV=three Ad-sig-ecdhMUC-1/ΔCtΔTm CD40L vector subcutaneous injections administered on days 1, 7 and 21; PPP=three ecdhMUC-1/ΔCtΔTm CD40L protein subcutaneous injections administered on days 1, 7 and 21; or VPP=a single Ad-sig-ecdhMUC-1/ΔCtΔTm CD40L vector subcutaneous injection followed at days 7 and 21 by ecdhMUC-1/ΔCtΔTm CD40L protein subcutaneous injections. One week later (day 28), mice were injected subcutaneously with five hundred thousand LL2/LL1hMUC-1 lung cancer cells. Two weeks later (day 42), 500,000 of the LL2/LL1hMUC-1 tumor cells were administered intravenously to test mice via the tail vein. Multiple administrations of vector alone or vector followed by boosting with protein was effective in preventing the establishment of human tumors in mice.

FIG. 7 shows that three injections of the fusion protein (PPP) without a preceding Ad-sig-ecdhMUC-1/ecdCD40L vector injection failed to induce complete resistance to the development of the subcutaneous LL2/LL1hMUC-1 tumor. In contrast, the schedule of three successive vector injections (VVV) or one vector injection followed by two protein injections (VPP) completely suppressed the appearance of the subcutaneous LL2/LL1hMUC-1 tumor.

Figure 8:
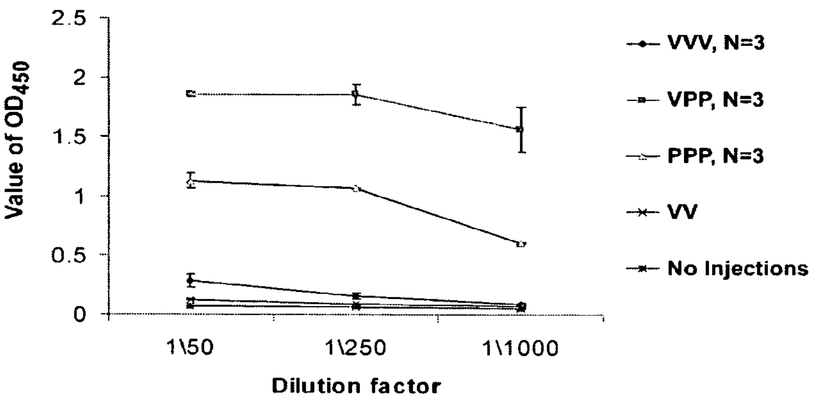
FIG. 8 demonstrates the levels of hMUC-1 specific antibodies in vaccinated test mice at 63 days following the start of the vaccination. VVV=three Ad-sig-ecdhMUC-1/ΔCtΔTm CD40L vector subcutaneous injections administered on days 1, 7 and 21; PPP=three ecdhMUC-1/ΔCtΔTm CD40L protein subcutaneous injections administered on days 1, 7 and 21; or VPP=a single Ad-sig-ecdhMUC-1/ΔCtΔTm CD40L vector subcutaneous injection followed at days 7 and 21 by ecdhMUC-1/ΔCtΔTm CD40L protein subcutaneous injections. The schedule of one Ad-sig-ecdhMUC-1/deltaCtdeltaTmCD40L vector subcutaneous injection followed by two successive ecdhMUC-1/deltaCtdeltaTmCD40L protein subcutaneous injections at 7 and 21 days following the vector injection induced the highest levels of hMUC-1 specific antibodies.

The levels of hMUC-1 specific antibodies in these mice at 63 days following the start of the vaccination were measured (FIG. 8). The schedule of a single vector injection followed by two successive fusion protein boosts (VPP) induced the highest levels of hMUC-1 specific antibodies, schedule VVV was intermediate, and schedule VPP was virtually ineffective. Thus, cancer therapy in these animals related somewhat inversely to the antibody response.

A tumor treatment (post establishment) protocol was also evaluated. In this schedule, subcutaneous tumor (500,000 of the LL2/LL1hMUC-1) was administered on day 1. The three schedules (PPP, VPP and VVV) were accomplished on days 5, 12 and 26. Tumor was administered i.v. on day 35 and tumor development (subcutaneous and lung) evaluated at day 49. Further details are found in the legend to FIG. 9.

Figure 9:
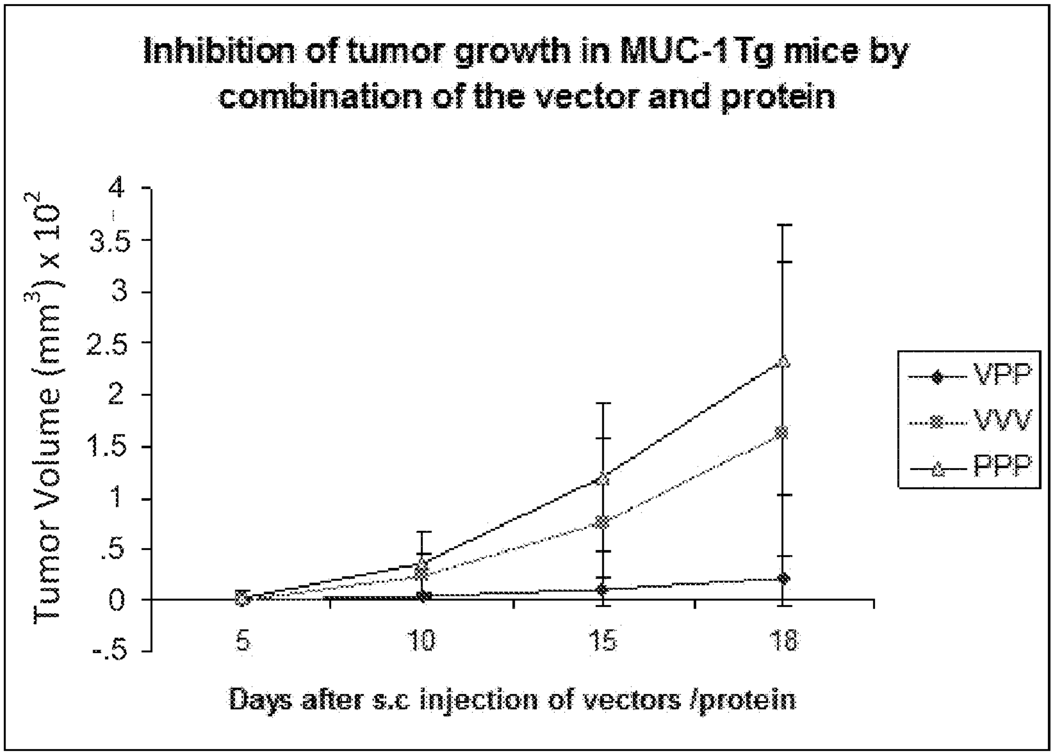
FIG. 9 demonstrates subcutaneous tumor therapy (post establishment) in animals immunized with Ad-sig-ecdhMUC-1/ΔCtΔTmCD40L vector and ecdhMUC-1/ΔCtΔTm CD40L protein. VVV=three Ad-sig-ecdhMUC-1/ΔCtΔTm CD40L vector subcutaneous injections administered on days 5, 12 and 26; PPP=three ecdhMUC-1/ΔCtΔTm CD40L protein subcutaneous injections administered on days 5, 12 and 26; or VPP=a single Ad-sig-ecdhMUC-1/ΔCtΔTm CD40L vector subcutaneous injection followed at days 12 and 26 by ecdhMUC-1/ΔCtΔTm CD40L protein subcutaneous injections. Subcutaneous tumor (500,000 of the LL2/LL1hMUC-1) was administered on day 1 and vaccinations were carried out at day 5. Tumor was administered i.v. on day 40 and tumor development (subcutaneous and lung) evaluated at day 54.

As shown in FIG. 9, the combination of one vector injection followed by two protein injections (VPP) completely suppressed the growth of established subcutaneous hMUC-1 positive cancer cell tumor. Three successive vector administrations (VVV) had a small therapeutic affect while three successive protein injections (PPP) had little to no effect.

Figure 10:
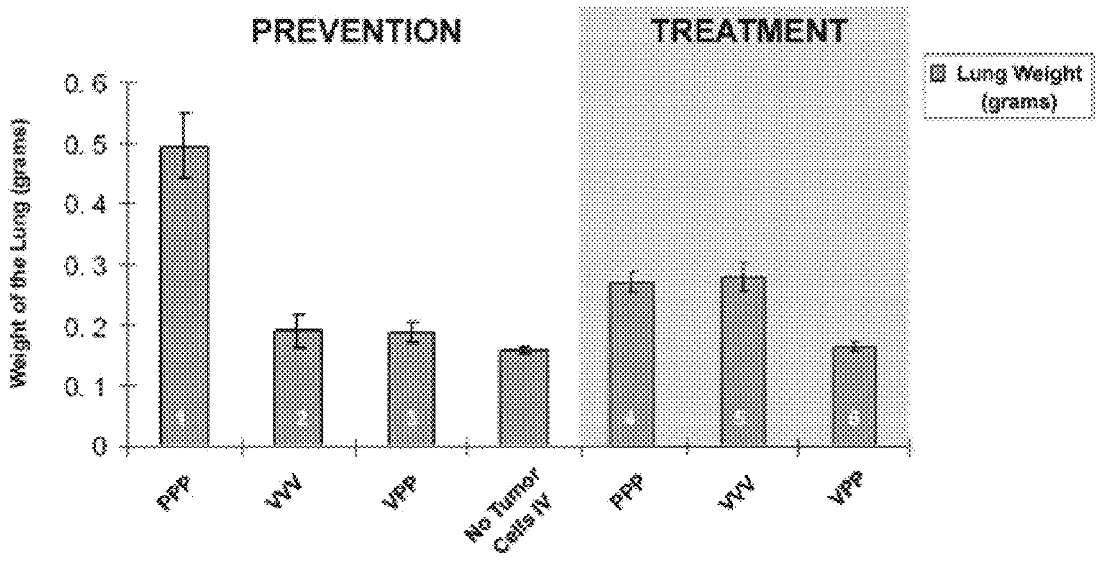
FIG. 10 demonstrates lung metastatic tumor nodule therapy (post establishment) in the animals treated as described in FIG. 9. Left panel: The results were similar to the subcutaneous tumor prevention with schedule VVV and VPP most effective. Right panel: the combination of one vector injection followed by two protein injections (VPP) completely suppressed the growth of established lung nodules of the hMUC-1 positive cancer cells.

The growth of metastatic lung nodules in the pretreatment and post-treatment (pre-establishment) cancer models is shown in FIG. 10. The pretreatment results in FIG. 10, left hand panel show that three successive fusion protein injections (PPP) did not appear to suppress lung nodule growth. In contrast, schedule VVV and schedule VPP appeared to completely suppress the engraftment of the lung cancer in the lungs of the vaccinated animals.

The post treatment results in FIG. 10, right hand panel show that the combination of one vector injection followed by two protein injections (VPP) completely suppressed the growth of established lung nodules of the hMUC-1 positive cancer cells. In contrast, three successive vector administrations (VVV) and three successive protein injections (PPP) showed some therapeutic effect but less than for the VPP protocol.

These results suggest that the best overall cancer therapy schedule is the VPP schedule, involving a single injection of Ad-sig-ecdhMUC-1/ecdCD40L vector followed in one week by two successive subcutaneous injections, spaced two weeks apart, of the ecdhMUC-1/ecdCD40L protein. This protocol is characterized by induction of antibody (humoral immunity) and T cell immunity (cellular immunity) to the mucin antigen.

Figure 11:
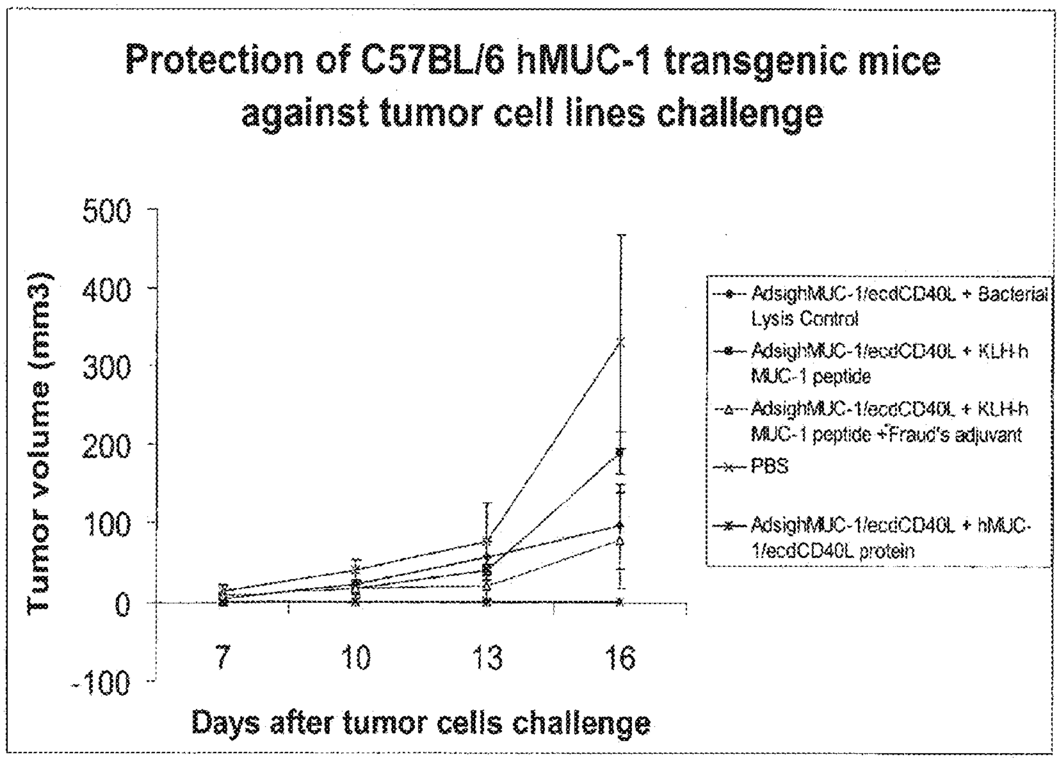

Boosting with ecdMUC-1/ecdCD40L soluble protein versus other soluble proteins following a primary administration of the adenoviral expression vector encoding the same protein was evaluated in hMUC-1.Tg animals challenged with MUC-1 expressing tumor (LL2/LL1hMUC-1 cell line). Animals were boosted with a bacterial extract containing ecdMUC-1/ecdCD40 (from a bacterial host strain infected with Ad-sig-ecdMUC-1/ecdCD40L vector); ecdMUC-1 linked to the keyhole limpet hemocyaninin (KLH), with or without incomplete Freund's adjuvant; PBS; and control bacterial extract (from a bacterial host strain not infected with Ad-sig-ecdMUC-1/ecdCD40L vector). The tumor cells were given 7 days following the completion of the 2nd protein boost. The results shown in FIG. 11 indicate that boosting with ecdMUC-1/ecdCD40L soluble protein was superior to all other approaches.

6. Construction of Adenoviral Vectors Encoding HPV E7-CD40 Ligand Fusion Protein.

Methods of generating immunity by administering and adenoviral vector expressing a transcription unit fusion protein constituting E7 linked to a secretable form of CD40 ligand was recently reported. Ziang et al., "An adenoviral vector cancer vaccine that delivers a tumor-associated antigen/CD40-ligand fusion protein to dendritic cells" Proc. Natl. Acad. Sci (USA) published Nov. 25, 2003, 10.1073/pnas.2135379100 (vol. 100(25):15101).

The transcription unit included DNA encoding the signal peptide from the HGH gene upstream of DNA encoding the full length HPV type 16 E7 protein upstream of ΔCtΔTmCD40L. DNA encoding the human growth hormone signal sequence MATGSRTSLLLAFGLLCLPWLQEGSA (single letter amino acid code) (SEQ ID NO: 32) was prepared by annealing phosphorylated oligonucleotides (SEQ ID NOs:33 and 34) to generate the full 26 amino acid HGH sequence with Bg1 II and Not1 overhangs.

Growth hormone signal upper strand
(coding sequence in italics):
(SEQ ID NO: 33)
5'-GATCT CCACC *ATG GCT ACA GGC TCC CGG ACG TCC CTG*
*CTC CTG GCT TTT GGC CTG CTC TGC CTG CCC TGG CTT*
*CAA GAG GGC AGT GCC GGC*-3'

Growth hormone signal lower strand:
(SEQ ID NO: 34)
3'-A GGTGG TAC CGA TGT CCG AGG GCC TGC AGG GAC GAG
GAC CGA AAA CCG GAC GAG ACG GAC GGG ACC GAA GTT
CTC CCG TCA CGG CCGCCGG-5'.

Synthetic HGH signal sequence was prepared by annealing the above upper and lower strand oligos. The oligos were dissolved in 50 μl $H_2O$ (about 3 mg/ml). 1 μl from each oligo (upper and lower strand) was added to 48 μl annealing buffer (100 mM potassium acetate, 30 mM HEPES-KOH pH 7.4, and 2 mM Mg-acetate) incubated at 4 minutes at 95° C., 10 minutes at 70° C. and slowly cooled to about 4° C. The annealed DNA was phosphorylated using T4 PNK (polynucleotide kinase) under standard conditions.

The HGH signal sequence with Bg1 II and Not I overhangs was inserted via Bg1 II and Not I into pShuttle-E7-ΔCtΔTmCD40L(no signal sequence) to yield pshuttle-HGH/E7-ΔCtΔTmCD40L. pShuttle-E7-ΔCtΔTmCD40L (no signal sequence) was prepared by inserting HPV-16 E7 upstream of the CD40 ligand sequence as follows: Sequence encoding the full HPV-16 E7 protein was obtained by PCR amplifying from the HPV viral genome using the following primers:

HPV 16 E 7 forward primer
(SEQ ID NO: 35)
5'-ATTT GCGGCCGC TGTAATCATGCATGGAGA-3'

HPV E7 reverse primer
(SEQ ID NO: 36)
5-CC CTCGAG TTATGGTTTCTGAGAACAGAT-3'

The resulting amplicon was HPV 16 E 7 encoding DNA with 5' end Not I and 3' end Xho 1 restriction sites. The E7 DNA was inserted into the pShuttleΔCtΔTmCD40L between the CMV promoter and directly 5' to the spacer of the ΔCtΔTMCD40L sequence using Not I (GCGGCCGC) and Xho I (CTCGAG). The plasmid is designated pShuttle-E7-ΔCtΔTmCD40L (no signal sequence) and was used for insertion of the HGH signal sequence upstream of E7 to generate HGH/E7-ΔCtΔTmCD40L as already described. Thus, the transcription unit HGH/E7-ΔCtΔTmCD40L encodes the HGH secretory signal followed by the full length HPV type 16 E7 followed by a 10 amino acid linker with (FENDAQAPKS; SEQ ID NO: 37) followed by murine CD40 ligand residues 52-260.

A transcription unit that included DNA encoding the signal sequence of the mouse IgG kappa chain gene upstream of DNA encoding the full length HPV type 16 E7 protein ("K/E7") was generated by PCR using HPV16 plasmid and the following primers:

(primer 1)
(SEQ ID NO: 38)
5'-ACG ATG GAG ACA GAC ACA *CTC CTG CTA TGG GTA CTG*
*CTG*-3'

(primer 2)
(SEQ ID NO: 39)
5'-TC CTG CTA TGG GTA CTG CTG CTC *TGG GTT CCA GGT*
*TC*-3'

(primer 3)
(SEQ ID NO: 40)
5'-TG CTC TGG GTT CCA *GGT TCC ACT GGT GAC ATG CAT*
*G*-3';

(primer 4)
(SEQ ID NO: 41)
5'-TGG GTT CCA GGT TCC ACT GGT GAC ATG CAT GGA G
AT ACA CCT AC-3';
and (primer 5)
(SEQ ID NO: 42)
5'-CCG CTC GAG TGG TTT CTG AGA ACA GAT GGG GCA
C-3.'

K/E7 with the upstream kappa signal sequence was generated by four rounds of PCR amplification ($1^{st}$ round: primers 4+5; $2^{nd}$ round: add primer 3; $3^{rd}$ round: add primer 2; $4^{th}$ round: add primer 1). The K/E7 encoding DNA was cloned into the pcDNA™ 3.1 TOPO vector (Invitrogen, San Diego, Calif.) forming pcDNA-K/E7.

A DNA fragment that contained the mouse CD40 ligand from which the transmembrane and cytoplasmic domain had been deleted (ΔCtΔTmCD40L) was generated from a mouse CD40 ligand cDNA Plasmid (pDC406-mCD40L; ATCC) using the following PCR primers:

(SEQ ID NO: 43)
5'-CCG CTCGAG *AAC GAC GCA CAA GCA CCA AAA AGC* AAG
GTC GAA GAG GAA GTA AAC CTT C-3';
and (SEQ ID NO: 44)
5'-CGCGCCGCGCGCTAG *TCTAGA* GAGTTTGAGTAAGCCAAAAGATG
AG-3'
(high fidelity PCR kit, Roche).

Fragment ΔCtΔTmCD40L was digested with Xba I and XhoI restriction endonucleases and then ligated into pcDNA-E7. K/E7-ΔCtΔTmCD40L fragment was cut from the pcDNA vector and inserted into the pShuttle plasmid using Hind III and Xba I sites (pShuttle K/E7-CtΔTmCD40L). Thus, the K/E7-ΔCtΔTmCD40L fragment includes the kappa chain secretory signal followed by the full length HPV type 16 E7 followed by a 10 amino acid linker (LQNDAQAPKS; SEQ ID NO: 52) followed by murine CD40 ligand residues 52-260.

A vector encoding E7 fused to human CD40 ligand lacking a transmembrane domain is prepared by inserting "space+ΔCtΔTmCD40L(human)" (prepared as described above) into the plasmid pShuttle-CMV (13) after restriction endonuclease digestion with Hind III (AAGCTT) and Xho I (CTC-GAG). This vector is designated pShuttleΔCtΔTmCD40L (human). Modification of pShuttleΔCtΔTmCD40L(human) to include the HPV-16 E7 upstream of the human CD40 ligand sequence was accomplished essentially as described above for the murine CD40 ligand encoding vectors. The resulting plasmid is designated pShuttle-E7-ΔCtΔTmCD40L (human)(no signal sequence) and is used for insertion of the HGH signal sequence upstream of E7 to generate HGH/E7-ΔCtΔTmCD40L(human). Thus, the transcription unit HGH/E7-ΔCtΔTmCD40L(human) encodes the HGH secretory signal followed by the full length HPV type 16 E7 followed by a 10 amino acid linker (FENDAQAPKS; SEQ ID NO:37) followed by human CD40 ligand residues 47-261.

7. Construction of Adenoviral Vectors Encoding ratHER2 (Neu)/CD40L

The overexpression of the Her-2-Neu (H2N) growth factor receptor in 30% of breast cancers is associated with increased frequency of recurrence after surgery, and shortened survival. Mice transgenic for the rat equivalent of HER2 ("H2N" or "rH2N") gene and therefore tolerant of this gene (Muller et al., *Cell* 54: 105-115, (1998); Gut et al. *Proc. Natl. Acad. Sci.* USA 89: 10578-10582, (1992)) were used as experimental hosts for evaluating immunity in the Ad-sig-rH2N/ecdCD40L vector. In this model, the mouse is made transgenic for a normal unactivated rat Her-2-Neu gene under the control of a mammary specific transcriptional promoter such as the MMTV promoter. The MMTV promoter produces overexpression of a non-mutant rat Her-2-Neu receptor, which is analogous to what occurs in human breast cancer. This model produces palpable tumor nodules in the primary tissue (the breast) at 24 weeks as well as pulmonary metastases at 32 weeks. The development of breast cancer occurs spontaneously. The cancer begins focally as a clonal event in the breast epithelial tissue through a step-wise process (Id.). Dysplasia can be detected by 12 weeks of birth. Palpable tumors in the mammary glands can be detected at 25 weeks, and metastatic breast cancer in the lung can be demonstrated in 70% of mice by 32 weeks (Id.).

Ad-sig-rH2N/ecdCD40L vector was subcutaneously administered to transgenic animals one or two times at 7 day intervals to test if an immune response could be induced against the rat Her-2-Neu antigen. Two subcutaneous injections of the Ad-sig-rH2N/ecdCD40L vector induced complete resistance to the growth of the N202 (rH2N positive) mouse breast cancer cell line, whereas one subcutaneous injection of the same vector did not induce sufficient immune response to completely suppress the growth of the rH2N positive N202 cell line. ELISPOT assays showed that the administration of two subcutaneous injections of the Ad-sig-rH2N/ecdCD40L vector 7 days apart induced levels of rH2N specific T cells in the spleens of vaccinated mice which were 10 times higher than the levels of rH2N specific T cells induced in mice following one injection of the Ad-sig-rH2N/ecdCD40L vector. Finally, the immune resistance induced against the NT2 cells by the Ad-sig-rH2N/ecdCD40L vector prime vaccination was better than the response obtained in transgenic animals vaccinated with irradiated cytokine positive tumor cells (mitomycin treated NM cells which had been transfected with a GMCSF transcription unit).

The rH2N specific antibody levels were also measured in mice vaccinated with one or two subcutaneous injections of the Ad-sig-rH2N/ecdCD40L vector. The levels of the rH2N specific antibody levels were higher following two subcutaneous injections than following a single subcutaneous injection of the Ad-sig-rH2N/ecdCD40L vector.

8. Construction of Adenoviral Vectors Encoding huHER2/CD40L

An adenoviral vector encoding sig ecdhuHER2/CD40L was prepared as follows. The mouse IgG kappa chain METDTLLLWVLLLWVPGSTGD (single letter amino acid code) (SEQ ID NO: 11) was prepared by PCR amplification (SEQ ID NOs: 12, 13 and 45) to generate the full 21 amino acid mouse IgG kappa chain signal sequence (the start codon "ATG" is shown bolded in SEQ ID NO:12).

```
                                        (SEQ ID NO: 12)
5'-CCACC ATG GAG ACA GAC ACA CTC CTG CTA TGG GTA

CTG CTG-3'

                                        (SEQ ID NO: 13)
5'-TC CTG CTA TGG GTA CTG CTG CTC TGG GTT CCA GGT

TC-3'


The forward primer
                                        (SEQ ID NO: 45)
5'-5'-TG CTC TGG GTT CCA GGT TCC ACT GGT GAC GAA

CTC-3'

The forward primer for the human HER2
extracellular domain
                                        (SEQ ID NO: 46)
5'-TCC ACT GGT GAC GAACTCACCTACCTGCCCACCAATGC-3'

The reverse Primer for the human HER2
extracellular domain
                                        (SEQ ID NO: 47)
5'-GGAGCTCGAG GGCTGGGTCCCCATCAAAGCTCTC-3'
```

sig-ecdhHER2 with the upstream kappa signal sequence is generated by four rounds of PCR amplification (1" round: primers SEQ ID NOs 46 and 47; 2$^{nd}$ round: primer SEQ ID NOs 45 and 47; 3$^{rd}$ round: primer SEQ ID NOs 13 and 47; 4$^{th}$ round: primer SEQ ID NOs 12 and 47). The sig-ecdhHER2 encoding DNA can be cloned into the pcDNA™ 3.1 TOPO vector (Invitrogen, San Diego, Calif.) forming pcDNA-sig-ecdhHER2. The additional cloning steps described for the MUC-1/CD40 Ligand expression vector are also applicable for the HER2/CD40 ligand expression vector.

This region HER2 extracellular domain to be fused to CD40 ligand contains two CTL epitopes; One is an HLA-A2 peptide, K I F G S L A F L (SEQ ID NO:48) representing amino acids 369-377. This peptide elicited short-lived peptide-specific immunity in HER2 expressing cancer patients. See Knutson et al., Immunization of cancer patients with a HER-2/neu, HLA-A2 peptide, Clin Cancer Res. 2002 May; 8(5):1014-8p369-377. The second epitope is E L T Y L P T N A S (SEQ ID NO: 49) (HER2 residues 63-71) also was useful in generating immunity to HER2 expressing tumor cells. See Wang et al. Essential roles of tumor-derived helper T cell epitopes for an effective peptide-based tumor vaccine, Cancer Immun. 2003 Nov 21;3:16. The region of the HER2 ecd also includes a B cell epitope P L H N Q E V T A E D G T Q R C E K C S K P (SEQIDNO:50)(HER2 positions 316-339). See Dakappagari et al., Chimeric multi-human epidermal growth factor receptor-2 B cell epitope peptide vaccine mediates superior antitumor responses, J Immunol. 2003 Apr. 15; 170 (8):4242-53.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein.

Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method of generating an immune response for the purpose of treating existing tumor growth in an individual against a MUC1 tumor antigen, comprising:

a) a first step of administering on day one to the individual an effective amount of an adenoviral viral expression vector, said vector comprising a transcription unit encoding a secretable fusion protein, said fusion protein comprising a secretory signal sequence, a MUC1 tumor antigen and a CD40 ligand wherein said CD40 ligand does not include a transmembrane domain and wherein said fusion protein is oriented with the tumor antigen attached to the N-terminus of the extracellular domain of said CD40 ligand;

b) a second step of administering a first boost one week from administration of the expression vector, a composition that comprises an effective amount of the secretable fusion protein comprising the MUC1 tumor antigen and CD40 ligand; and c) a third step of administering a second boost three weeks from administration of the expression vector, a composition that comprises an effective amount of the secretable fusion protein comprising the MUC1 tumor antigen and CD40 ligand.

2. The method according to claim 1 wherein said three steps are adapted to generate cytotoxic T cell activity to the MUC1 tumor antigen.

3. The method according to claim 2 wherein said three steps are adapted to additionally generate antibody responses to the MUC1 tumor antigen.

4. The method according to claim 1 wherein said second step, the first boost is an effective amount of said adenoviral expression vector.

5. A method of generating an immune response for the purpose of both, generating enhanced cytotoxic T cell activity and enhanced antibody activity, in an individual, against a MUC1 tumor antigen, comprising:

a) a first step of administering on day one to the individual an effective amount of an adenoviral viral expression vector, said vector comprising a transcription unit encoding a secretable fusion protein, said fusion protein comprising a secretory signal sequence a MUC1 tumor antigen and a CD40 ligand wherein said CD40 ligand does not include a transmembrane domain and wherein said fusion protein is oriented with the tumor antigen attached to the N-terminus of the extracellular domain of said CD40 ligand;

b) a second step of administering a first boost one week from the administration of the expression vector a composition that comprises an effective amount of a fusion protein comprising the MUC1 tumor antigen and CD40 ligand; and c) a third step of administering a second boost three weeks from administration of the expression vector a composition that comprises an effective amount of the fusion protein applied via the first boost.

* * * * *

SEQUENCE LISTING

```
<160> NUMBER OF SEQ ID NOS: 52

<210> SEQ ID NO 1
<211> LENGTH: 4139
<212> TYPE: DNA
<213> ORGANISM: Homo sapiens

<400> SEQUENCE: 1

ccgctccacc tctcaagcag ccagcgcctg cctgaatctg ttctgccccc tccccaccca      60

tttcaccacc accatgacac cgggcaccca gtctcctttc ttcctgctgc tgctcctcac     120

agtgcttaca gttgttacag gttctggtca tgcaagctct accccaggtg gagaaaagga     180

gacttcggct acccagagaa gttcagtgcc cagctctact gagaagaatg ctgtgagtat     240

gaccagcagc gtactctcca gccacagccc cggttcaggc tcctccacca ctcagggaca     300

ggatgtcact ctggccccgg ccacggaacc agcttcaggt tcagctgcca cctggggaca     360

ggatgtcacc tcggtcccag tcaccaggcc agccctgggc tccaccaccc cgccagccca     420

cgatgtcacc tcagccccgg acaacaagcc agccccgggc tccaccgccc ccccagccca     480

cggtgtcacc tcggccccgg acaccaggcc ggccccgggc tccaccgccc ccccagccca     540

cggtgtcacc tcggccccgg acaccaggcc ggccccgggc tccaccgccc ccccagccca     600

cggtgtcacc tcggccccgg acaccaggcc ggccccgggc tccaccgccc ccccagccca     660

cggtgtcacc tcggccccgg acaccaggcc ggccccgggc tccaccgccc ccccagccca     720

cggtgtcacc tcggccccgg acaccaggcc ggccccgggc tccaccgccc ccccagccca     780

cggtgtcacc tcggccccgg acaccaggcc ggccccgggc tccaccgccc ccccagccca     840

cggtgtcacc tcggccccgg acaccaggcc ggccccgggc tccaccgccc ccccagccca     900

cggtgtcacc tcggccccgg acaccaggcc ggccccgggc tccaccgccc ccccagccca     960

cggtgtcacc tcggccccgg acaccaggcc ggccccgggc tccaccgccc ccccagccca    1020

cggtgtcacc tcggccccgg acaccaggcc ggccccgggc tccaccgccc ccccagccca    1080

cggtgtcacc tcggccccgg acaccaggcc ggccccgggc tccaccgccc ccccagccca    1140

cggtgtcacc tcggccccgg acaccaggcc ggccccgggc tccaccgccc ccccagccca    1200

cggtgtcacc tcggccccgg acaccaggcc ggccccgggc tccaccgccc ccccagccca    1260

cggtgtcacc tcggccccgg acaccaggcc ggccccgggc tccaccgccc ccccagccca    1320

cggtgtcacc tcggccccgg acaccaggcc ggccccgggc tccaccgccc ccccagccca    1380

cggtgtcacc tcggccccgg acaccaggcc ggccccgggc tccaccgccc ccccagccca    1440

cggtgtcacc tcggccccgg acaccaggcc ggccccgggc tccaccgccc ccccagccca    1500

cggtgtcacc tcggccccgg acaccaggcc ggccccgggc tccaccgccc ccccagccca    1560

cggtgtcacc tcggccccgg acaccaggcc ggccccgggc tccaccgccc ccccagccca    1620

cggtgtcacc tcggccccgg acaccaggcc ggccccgggc tccaccgccc ccccagccca    1680

cggtgtcacc tcggccccgg acaccaggcc ggccccgggc tccaccgccc ccccagccca    1740
```

-continued cggtgtcacc tcggccccgg acaccaggcc ggccccgggc tccaccgccc ccccagccca 1800
cggtgtcacc tcggccccgg acaccaggcc ggccccgggc tccaccgccc ccccagccca 1860
cggtgtcacc tcggccccgg acaccaggcc ggccccgggc tccaccgccc ccccagccca 1920
cggtgtcacc tcggccccgg acaccaggcc ggccccgggc tccaccgccc ccccagccca 1980
cggtgtcacc tcggccccgg acaccaggcc ggccccgggc tccaccgccc ccccagccca 2040
cggtgtcacc tcggccccgg acaccaggcc ggccccgggc tccaccgccc ccccagccca 2100
cggtgtcacc tcggccccgg acaccaggcc ggccccgggc tccaccgccc ccccagccca 2160
cggtgtcacc tcggccccgg acaccaggcc ggccccgggc tccaccgccc ccccagccca 2220
cggtgtcacc tcggccccgg acaccaggcc ggccccgggc tccaccgccc ccccagccca 2280
cggtgtcacc tcggccccgg acaccaggcc ggccccgggc tccaccgccc ccccagccca 2340
cggtgtcacc tcggccccgg acaccaggcc ggccccgggc tccaccgccc ccccagccca 2400
cggtgtcacc tcggccccgg acaccaggcc ggccccgggc tccaccgccc ccccagccca 2460
cggtgtcacc tcggccccgg acaccaggcc ggccccgggc tccaccgccc ccccagccca 2520
cggtgtcacc tcggccccgg acaccaggcc ggccccgggc tccaccgccc ccccagccca 2580
cggtgtcacc tcggccccgg acaccaggcc ggccccgggc tccaccgccc ccccagccca 2640
cggtgtcacc tcggccccgg acaccaggcc ggccccgggc tccaccgccc ccccagccca 2700
cggtgtcacc tcggccccgg acaccaggcc ggccccgggc tccaccgccc ccccagccca 2760
cggtgtcacc tcggccccgg acaccaggcc ggccccgggc tccaccgccc ccccagccca 2820
cggtgtcacc tcggccccgg acaccaggcc ggccccgggc tccaccgccc ccccagccca 2880
tggtgtcacc tcggccccgg acaacaggcc cgccttgggc tccaccgccc ctccagtcca 2940
caatgtcacc tcggcctcag gctctgcatc aggctcagct tctactctgg tgcacaacgg 3000
cacctctgcc agggctacca caaccccagc cagcaagagc actccattct caattcccag 3060
ccaccactct gatactccta ccacccttgc cagccatagc accaagactg atgccagtag 3120
cactcaccat agctcggtac ctcctctcac ctcctccaat cacagcactt ctccccagtt 3180
gtctactggg gtctctttct ttttcctgtc ttttcacatt tcaaacctcc agtttaattc 3240
ctctctggaa gatcccagca ccgactacta ccaagagctg cagagagaca tttctgaaat 3300
gtttttgcag atttataaac aagggggttt tctgggcctc tccaatatta agttcaggcc 3360
aggatctgtg gtggtacaat tgactctggc cttccgagaa ggtaccatca atgtccacga 3420
cgtggagaca cagttcaatc agtataaaac ggaagcagcc tctcgatata acctgacgat 3480
ctcagacgtc agcgtgagtg atgtgccatt tcctttctct gcccagtctg gggctggggt 3540
gccaggctgg ggcatcgcgc tgctggtgct ggtctgtgtt ctggttgcgc tggccattgt 3600
ctatctcatt gccttggctg tctgtcagtg ccgccgaaag aactacgggc agctggacat 3660
ctttccagcc cgggatacct accatcctat gagcgagtac cccacctacc acacccatgg 3720
gcgctatgtg ccccctagca gtaccgatcg tagcccctat gagaaggttt ctgcaggtaa 3780
cggtggcagc agcctctctt acacaaaccc agcagtggca gccgcttctg ccaacttgta 3840
gggcacgtcg ccgctgagct gagtggccag ccagtgccat tccactccac tcaggttctt 3900
caggccagag cccctgcacc ctgtttgggc tggtgagctg ggagttcagg tgggctgctc 3960
acagcctcct tcagaggccc caccaatttc tcggacactt ctcagtgtgt ggaagctcat 4020
gtgggcccct gaggctcatg cctgggaagt gttgtggggg ctcccaggag gactggccca 4080
gagagccctg agatagcggg gatcctgaac tggactgaat aaaacgtggt ctcccactg 4139

<210> SEQ ID NO 2
<211> LENGTH: 1255
<212> TYPE: PRT
<213> ORGANISM: Homo sapiens

<400> SEQUENCE: 2

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380
```

-continued

```
Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800
```

-continued

```
Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
    850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp  Thr Pro Thr Thr Leu  Ala Ser His
        995                 1000                1005

Ser Thr  Lys Thr Asp Ala Ser  Ser Thr His His Ser  Ser Val Pro
    1010                 1015                 1020

Pro Leu  Thr Ser Ser Asn His  Ser Thr Ser Pro Gln  Leu Ser Thr
    1025                 1030                 1035

Gly Val  Ser Phe Phe Phe Leu  Ser Phe His Ile Ser  Asn Leu Gln
    1040                 1045                 1050

Phe Asn  Ser Ser Leu Glu Asp  Pro Ser Thr Asp Tyr  Tyr Gln Glu
    1055                 1060                 1065

Leu Gln  Arg Asp Ile Ser Glu  Met Phe Leu Gln Ile  Tyr Lys Gln
    1070                 1075                 1080

Gly Gly  Phe Leu Gly Leu Ser  Asn Ile Lys Phe Arg  Pro Gly Ser
    1085                 1090                 1095

Val Val  Val Gln Leu Thr Leu  Ala Phe Arg Glu Gly  Thr Ile Asn
    1100                 1105                 1110

Val His  Asp Val Glu Thr Gln  Phe Asn Gln Tyr Lys  Thr Glu Ala
    1115                 1120                 1125

Ala Ser  Arg Tyr Asn Leu Thr  Ile Ser Asp Val Ser  Val Ser Asp
    1130                 1135                 1140

Val Pro  Phe Pro Phe Ser Ala  Gln Ser Gly Ala Gly  Val Pro Gly
    1145                 1150                 1155

Trp Gly  Ile Ala Leu Leu Val  Leu Val Cys Val Leu  Val Ala Leu
    1160                 1165                 1170

Ala Ile  Val Tyr Leu Ile Ala  Leu Ala Val Cys Gln  Cys Arg Arg
    1175                 1180                 1185

Lys Asn  Tyr Gly Gln Leu Asp  Ile Phe Pro Ala Arg  Asp Thr Tyr
    1190                 1195                 1200
```

-continued

```
His Pro  Met Ser Glu Tyr Pro  Thr Tyr His Thr His  Gly Arg Tyr
    1205                 1210                 1215

Val Pro  Pro Ser Ser Thr Asp  Arg Ser Pro Tyr Glu  Lys Val Ser
    1220                 1225                 1230

Ala Gly  Asn Gly Gly Ser Ser  Leu Ser Tyr Thr Asn  Pro Ala Val
    1235                 1240                 1245

Ala Ala  Ala Ser Ala Asn Leu
    1250                 1255


<210> SEQ ID NO 3
<211> LENGTH: 20
<212> TYPE: PRT
<213> ORGANISM: Homo sapiens

<400> SEQUENCE: 3

Pro Asp Thr Arg Pro Ala Pro Gly Ser Thr Ala Pro Pro Ala His Gly
1               5                   10                  15

Val Thr Ser Ala
            20


<210> SEQ ID NO 4
<211> LENGTH: 24
<212> TYPE: PRT
<213> ORGANISM: Homo sapiens

<400> SEQUENCE: 4

Pro Thr Thr Thr Pro Pro Ile Thr Thr Thr Thr Thr Val Thr Pro Thr
1               5                   10                  15

Pro Thr Pro Thr Gly Thr Gln Thr
            20


<210> SEQ ID NO 5
<211> LENGTH: 17
<212> TYPE: PRT
<213> ORGANISM: Homo sapiens

<400> SEQUENCE: 5

His Ser Thr Pro Ser Phe Thr Ser Ser Ile Thr Thr Thr Glu Thr Thr
1               5                   10                  15

Ser


<210> SEQ ID NO 6
<211> LENGTH: 16
<212> TYPE: PRT
<213> ORGANISM: Homo sapiens

<400> SEQUENCE: 6

Thr Ser Ser Ala Ser Thr Gly His Ala Thr Pro Leu Pro Val Thr Asp
1               5                   10                  15


<210> SEQ ID NO 7
<211> LENGTH: 8
<212> TYPE: PRT
<213> ORGANISM: Homo sapiens

<400> SEQUENCE: 7

Thr Thr Ser Thr Thr Ser Ala Pro
1               5
```

<210> SEQ ID NO 8
<211> LENGTH: 29
<212> TYPE: PRT
<213> ORGANISM: Homo sapiens

<400> SEQUENCE: 8

```
Ser Ser Thr Pro Gly Thr Ala His Thr Leu Thr Met Leu Thr Thr Thr
1               5                   10                  15

Ala Thr Thr Pro Thr Ala Thr Gly Ser Thr Ala Thr Pro
            20                  25
```

<210> SEQ ID NO 9
<211> LENGTH: 22
<212> TYPE: PRT
<213> ORGANISM: Homo sapiens

<400> SEQUENCE: 9

```
Thr Thr Ala Ala Pro Pro Thr Pro Ser Ala Thr Thr Pro Ala Pro Pro
1               5                   10                  15

Ser Ser Ser Ala Pro Gly
            20
```

<210> SEQ ID NO 10
<211> LENGTH: 41
<212> TYPE: PRT
<213> ORGANISM: Homo sapiens

<400> SEQUENCE: 10

```
Thr Ser Cys Pro Arg Pro Leu Gln Glu Gly Thr Pro Gly Ser Arg Ala
1               5                   10                  15

Ala His Ala Leu Ser Arg Arg Gly His Arg Val His Glu Leu Pro Thr
            20                  25                  30

Ser Ser Pro Gly Gly Asp Thr Gly Phe
        35                  40
```

<210> SEQ ID NO 11
<211> LENGTH: 21
<212> TYPE: PRT
<213> ORGANISM: Mus musculus

<400> SEQUENCE: 11

```
Met Glu Thr Asp Thr Leu Leu Leu Trp Val Leu Leu Leu Trp Val Pro
1               5                   10                  15

Gly Ser Thr Gly Asp
            20
```

<210> SEQ ID NO 12
<211> LENGTH: 41
<212> TYPE: DNA
<213> ORGANISM: Artificial Sequence
<220> FEATURE:
<223> OTHER INFORMATION: Synthetic primer

<400> SEQUENCE: 12

```
ccaccatgga gacagacaca ctcctgctat gggtactgct g                         41
```

<210> SEQ ID NO 13
<211> LENGTH: 37
<212> TYPE: DNA
<213> ORGANISM: Artificial Sequence
<220> FEATURE:
<223> OTHER INFORMATION: Synthetic primer

<400> SEQUENCE: 13
tcctgctatg ggtactgctg ctctgggttc caggttc 37

<210> SEQ ID NO 14
<211> LENGTH: 33
<212> TYPE: DNA
<213> ORGANISM: Artificial Sequence
<220> FEATURE:
<223> OTHER INFORMATION: Synthetic primer

<400> SEQUENCE: 14
tgctctgggt tccaggttcc actggtgacg atg 33

<210> SEQ ID NO 15
<211> LENGTH: 36
<212> TYPE: DNA
<213> ORGANISM: Artificial Sequence
<220> FEATURE:
<223> OTHER INFORMATION: Synthetic primer

<400> SEQUENCE: 15
ggttccactg gtgacgatgt cacctcggtc ccagtc 36

<210> SEQ ID NO 16
<211> LENGTH: 31
<212> TYPE: DNA
<213> ORGANISM: Artificial Sequence
<220> FEATURE:
<223> OTHER INFORMATION: Synthetic primer

<400> SEQUENCE: 16
gagctcgaga ttgtggactg gaggggcggt g 31

<210> SEQ ID NO 17
<211> LENGTH: 51
<212> TYPE: DNA
<213> ORGANISM: Artificial Sequence
<220> FEATURE:
<223> OTHER INFORMATION: Synthetic primer

<400> SEQUENCE: 17
ccgctcgaga acgacgcaca agcaccaaaa tcaaaggtcg aagaggaagt a 51

<210> SEQ ID NO 18
<211> LENGTH: 53
<212> TYPE: DNA
<213> ORGANISM: Artificial Sequence
<220> FEATURE:
<223> OTHER INFORMATION: Synthetic primer

<400> SEQUENCE: 18
gcgggcccgc ggccgccgct agtctagaga gtttgagtaa gccaaaagat gag 53

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Leu Glu Asn Asp Ala Gln Ala Pro Lys Ser
1 5 10

<210> SEQ ID NO 20
<211> LENGTH: 62
<212> TYPE: DNA
<213> ORGANISM: Artificial Sequence
<220> FEATURE:
<223> OTHER INFORMATION: Synthetic primer

<400> SEQUENCE: 20
aacaagctca ttcagttcct gatctcactg gtgggatcca acgacgcaca agcaccaaaa 60
tc 62

<210> SEQ ID NO 21
<211> LENGTH: 60
<212> TYPE: DNA
<213> ORGANISM: Artificial Sequence
<220> FEATURE:
<223> OTHER INFORMATION: Synthetic primer

<400> SEQUENCE: 21
agccttcggc agaagcatgc ccagcaacag aaagtcgtca acaagctcat tcagttcctg 60

<210> SEQ ID NO 22
<211> LENGTH: 46
<212> TYPE: DNA
<213> ORGANISM: Artificial Sequence
<220> FEATURE:
<223> OTHER INFORMATION: Synthetic primer

<400> SEQUENCE: 22
aatgaggctc tgtggcggga ggtggccagc cttcggcaga agcatg 46

<210> SEQ ID NO 23
<211> LENGTH: 61
<212> TYPE: DNA
<213> ORGANISM: Artificial Sequence
<220> FEATURE:
<223> OTHER INFORMATION: Synthetic primer

<400> SEQUENCE: 23
gatatcctca ggctcgagaa cgacgcacaa gcaccaaaag agaatgaggc tctgtggcgg 60
g 61

<210> SEQ ID NO 24
<211> LENGTH: 53
<212> TYPE: PRT
<213> ORGANISM: Artificial Sequence
<220> FEATURE:
<223> OTHER INFORMATION: Synthetic peptide

<400> SEQUENCE: 24

```
Leu Glu Asn Asp Ala Gln Ala Pro Lys Glu Asn Glu Ala Leu Trp Arg
1               5                   10                  15

Glu Val Ala Ser Phe Arg Gln Lys His Ala Gln Gln Gln Lys Val Val
            20                  25                  30

Asn Lys Leu Ile Gln Phe Leu Ile Ser Leu Val Gly Ser Asn Asp Ala
        35                  40                  45

Gln Ala Pro Lys Ser
    50
```

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Leu Glu Asn Asp Ala Gln Ala Pro Lys
1 5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Asn Asp Ala Gln Ala Pro Lys Ser
1 5

<210> SEQ ID NO 27
<211> LENGTH: 51
<212> TYPE: DNA
<213> ORGANISM: Artificial Sequence
<220> FEATURE:
<223> OTHER INFORMATION: Synthetic primer

<400> SEQUENCE: 27
ccgctcgaga acgacgcaca agcaccaaaa tcaaaggtcg aagaggaagt a 51

<210> SEQ ID NO 28
<211> LENGTH: 51
<212> TYPE: DNA
<213> ORGANISM: Artificial Sequence
<220> FEATURE:
<223> OTHER INFORMATION: Synthetic primer

<400> SEQUENCE: 28
atggtgatga tgaccggtac ggagtttgag taagccaaaa gatgagaagc c 51

<210> SEQ ID NO 29
<211> LENGTH: 49
<212> TYPE: DNA
<213> ORGANISM: Artificial Sequence
<220> FEATURE:
<223> OTHER INFORMATION: Synthetic primer

<400> SEQUENCE: 29
gtgctctaga tcagaattca tggtgatggt gatgatgacc ggtacggag 49

<210> SEQ ID NO 30
<211> LENGTH: 60
<212> TYPE: DNA
<213> ORGANISM: Artificial Sequence
<220> FEATURE:
<223> OTHER INFORMATION: Synthetic primer

<400> SEQUENCE: 30
ccgctcgaga acgacgcaca agcaccaaaa tcagtgtatc ttcatagaag gttggacaag 60

<210> SEQ ID NO 31
<211> LENGTH: 34
<212> TYPE: DNA
<213> ORGANISM: Artificial Sequence
<220> FEATURE:
<223> OTHER INFORMATION: Synthetic primer

<400> SEQUENCE: 31
ccctctagat cagagtttga gtaagccaaa ggac 34

<210> SEQ ID NO 32
<211> LENGTH: 26
<212> TYPE: PRT
<213> ORGANISM: Homo sapiens

<400> SEQUENCE: 32

Met Ala Thr Gly Ser Arg Thr Ser Leu Leu Leu Ala Phe Gly Leu Leu
1 5 10 15

Cys Leu Pro Trp Leu Gln Glu Gly Ser Ala
20 25

<210> SEQ ID NO 33
<211> LENGTH: 91
<212> TYPE: DNA
<213> ORGANISM: Homo sapiens

<400> SEQUENCE: 33
gatctccacc atggctacag gctcccggac gtccctgctc ctggcttttg gcctgctctg 60
cctgccctgg cttcaagagg gcagtgccgg c 91

<210> SEQ ID NO 34
<211> LENGTH: 91
<212> TYPE: DNA
<213> ORGANISM: Homo sapiens

<400> SEQUENCE: 34
aggtggtacc gatgtccgag ggcctgcagg gacgaggacc gaaaaccgga cgagacggac 60
gggaccgaag ttctcccgtc acggccgccg g 91

<210> SEQ ID NO 35
<211> LENGTH: 30
<212> TYPE: DNA
<213> ORGANISM: Artificial Sequence
<220> FEATURE:
<223> OTHER INFORMATION: Synthetic primer

<400> SEQUENCE: 35
atttgcggcc gctgtaatca tgcatggaga 30

<210> SEQ ID NO 36
<211> LENGTH: 29
<212> TYPE: DNA
<213> ORGANISM: Artificial Sequence
<220> FEATURE:
<223> OTHER INFORMATION: Synthetic primer

<400> SEQUENCE: 36
ccctcgagtt atggtttctg agaacagat 29

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide linker

<400> SEQUENCE: 37

Phe Glu Asn Asp Ala Gln Ala Pro Lys Ser
1 5 10

<210> SEQ ID NO 38
<211> LENGTH: 39
<212> TYPE: DNA
<213> ORGANISM: Artificial Sequence
<220> FEATURE:
<223> OTHER INFORMATION: Synthetic primer

<400> SEQUENCE: 38
acgatggaga cagacacact cctgctatgg gtactgctg 39

<210> SEQ ID NO 39
<211> LENGTH: 37
<212> TYPE: DNA
<213> ORGANISM: Artificial Sequence
<220> FEATURE:
<223> OTHER INFORMATION: Synthetic primer

<400> SEQUENCE: 39
tcctgctatg ggtactgctg ctctgggttc caggttc 37

<210> SEQ ID NO 40
<211> LENGTH: 36
<212> TYPE: DNA
<213> ORGANISM: Artificial Sequence
<220> FEATURE:
<223> OTHER INFORMATION: Synthetic primer

<400> SEQUENCE: 40
tgctctgggt tccaggttcc actggtgaca tgcatg 36

<210> SEQ ID NO 41
<211> LENGTH: 44
<212> TYPE: DNA
<213> ORGANISM: Artificial Sequence
<220> FEATURE:
<223> OTHER INFORMATION: Synthetic primer

<400> SEQUENCE: 41
tgggttccag gttccactgg tgacatgcat ggagatacac ctac 44

<210> SEQ ID NO 42
<211> LENGTH: 34
<212> TYPE: DNA
<213> ORGANISM: Artificial Sequence
<220> FEATURE:
<223> OTHER INFORMATION: Synthetic primer

<400> SEQUENCE: 42
ccgctcgagt ggtttctgag aacagatggg gcac 34

<210> SEQ ID NO 43
<211> LENGTH: 58
<212> TYPE: DNA
<213> ORGANISM: Artificial Sequence
<220> FEATURE:
<223> OTHER INFORMATION: Synthetic primer

<400> SEQUENCE: 43
ccgctcgaga acgacgcaca agcaccaaaa agcaaggtcg aagaggaagt aaaccttc 58

<210> SEQ ID NO 44
<211> LENGTH: 46
<212> TYPE: DNA
<213> ORGANISM: Artificial Sequence
<220> FEATURE:
<223> OTHER INFORMATION: Synthetic primer

<400> SEQUENCE: 44
cgcgccgcgc gctagtctag agagtttgag taagccaaaa gatgag 46

<210> SEQ ID NO 45
<211> LENGTH: 35
<212> TYPE: DNA
<213> ORGANISM: Artificial Sequence
<220> FEATURE:
<223> OTHER INFORMATION: Synthetic primer

<400> SEQUENCE: 45
tgctctgggt tccaggttcc actggtgacg aactc 35

<210> SEQ ID NO 46
<211> LENGTH: 38
<212> TYPE: DNA
<213> ORGANISM: Artificial Sequence
<220> FEATURE:
<223> OTHER INFORMATION: Synthetic primer

<400> SEQUENCE: 46
tccactggtg acgaactcac ctacctgccc accaatgc 38

<210> SEQ ID NO 47
<211> LENGTH: 34
<212> TYPE: DNA
<213> ORGANISM: Artificial Sequence
<220> FEATURE:
<223> OTHER INFORMATION: Synthetic primer

<400> SEQUENCE: 47
ggagctcgag ggctgggtcc ccatcaaagc tctc 34

<210> SEQ ID NO 48
<211> LENGTH: 9
<212> TYPE: PRT
<213> ORGANISM: Homo sapiens

<400> SEQUENCE: 48

Lys Ile Phe Gly Ser Leu Ala Phe Leu
1 5

<210> SEQ ID NO 49
<211> LENGTH: 10
<212> TYPE: PRT
<213> ORGANISM: Homo sapiens

<400> SEQUENCE: 49

Glu Leu Thr Tyr Leu Pro Thr Asn Ala Ser
1 5 10

<210> SEQ ID NO 50
<211> LENGTH: 23
<212> TYPE: PRT
<213> ORGANISM: Homo sapiens

<400> SEQUENCE: 50

Pro Leu His Asn Gln Glu Val Thr Ala Glu Asp Gly Thr Gln Arg Cys
1 5 10 15

Glu Lys Cys Ser Lys Pro Cys
20

-continued

```
<210> SEQ ID NO 51
<211> LENGTH: 20
<212> TYPE: PRT
<213> ORGANISM: Homo sapiens

<400> SEQUENCE: 51

Pro Asp Asn Lys Pro Ala Pro Gly Ser Thr Ala Pro Pro Ala His Gly
1               5                   10                  15

Val Thr Ser Ala
            20


<210> SEQ ID NO 52
<211> LENGTH: 10
<212> TYPE: PRT
<213> ORGANISM: Artificial Sequence
<220> FEATURE:
<223> OTHER INFORMATION: Synthetic peptide linker

<400> SEQUENCE: 52

Leu Gln Asn Asp Ala Gln Ala Pro Lys Ser
1               5                   10
```